(12) United States Patent
Ojima

(10) Patent No.: US 7,820,839 B2
(45) Date of Patent: Oct. 26, 2010

(54) TAXOID-FATTY ACID CONJUGATES AND PHARMACEUTICAL COMPOSITIONS THEREOF

(75) Inventor: Iwao Ojima, Port Jefferson, NY (US)

(73) Assignee: The Research Foundation of State University of New York, Albany, NY (US)

( * ) Notice: Subject to any disclaimer, the term of this patent is extended or adjusted under 35 U.S.C. 154(b) by 892 days.

(21) Appl. No.: 10/577,573

(22) PCT Filed: Oct. 28, 2004

(86) PCT No.: PCT/US2004/036027

§ 371 (c)(1),
(2), (4) Date: Dec. 22, 2006

(87) PCT Pub. No.: WO2005/041881

PCT Pub. Date: May 12, 2005

(65) Prior Publication Data

US 2007/0088076 A1    Apr. 19, 2007

Related U.S. Application Data

(60) Provisional application No. 60/515,783, filed on Oct. 30, 2003.

(51) Int. Cl.
*C07D 305/00* (2006.01)
*A61K 31/335* (2006.01)
*C07C 59/185* (2006.01)

(52) U.S. Cl. .................. 549/511; 549/510; 514/449; 554/118

(58) Field of Classification Search .......... 549/511, 549/510; 514/449, 444, 4; 554/118, 214
See application file for complete search history.

(56) References Cited

U.S. PATENT DOCUMENTS

| 5,795,909 A | 8/1998 | Shashoua et al. |
| 5,919,815 A | 7/1999 | Bradley et al. |
| 6,080,877 A | 6/2000 | Swindell et al. |
| 6,576,636 B2 | 6/2003 | Webb et al. |

FOREIGN PATENT DOCUMENTS

WO    WO 2005/041881 A2    5/2005

OTHER PUBLICATIONS

Bradley, et al. "Tumor Targeting by Covalent Conjugation of a Natural Fatty Acid to Paclitaxel" *Clinical Cancer Research* vol. 7:3229-3238 (2001).
Interview with Nigel Webb "Better Benefits, Fewer Risks", Pharmaceutical Executive May 2001.
Ojima, et al. "Synthesis and Structure-Activity Relationships of New Second-Generation Taxoids," *Bioorg. Med. Chem. Lett.*, 9:3423-3428 (1999).
Ojima, et al. "Synthesis and Struture-Activity Relationships of the Second-Generation Antitumor Taxoids: Exceptional Activity against Drug-Resistant Cancer Cells," *J. Med. Chem.* 39:3889-3896 (1996).
Vredenburg, et al. "Effects of Orally Active Taxanes on P-Glycoprotein Modulation and Colon and Breast Carcinoma Drug Resistance," Journal of the National Cancer Institute 93(16):1234-1245 (Aug. 2001).

*Primary Examiner*—Janet L. Andres
*Assistant Examiner*—Raymond Covington
(74) *Attorney, Agent, or Firm*—Hoffmann & Baron, LLP

(57) ABSTRACT

The invention relates to a second-generation-fatty acid conjugate and pharmaceutical compositions thereof. The second-generation-fatty acid conjugate are useful in the treatment of cancer in a human in need thereof.

71 Claims, 2 Drawing Sheets

TAXOID-FATTY ACID CONJUGATES AND PHARMACEUTICAL COMPOSITIONS THEREOF

This application asserts priority to U.S. Provisional Application Ser. No. 60/515,783 filed on Oct. 30, 2003, the specification of which is incorporated by reference in its entirety.

The invention described in this application was made with funds from the National Institutes of Health, Grant Numbers R01 GM427980 and R01 CA103314. The United States Government has certain rights in this invention.

BACKGROUND OF THE INVENTION

Paclitaxel (Taxol®) and docetaxel (Taxotère®) are two of the most important antitumor drugs approved for clinical use in chemotherapy against human tumors. Paclitaxel is a naturally occurring taxane, which was initially isolated from the bark of the Pacific yew tree, *Taxus brevifolia*.

Docetaxel is a semi-synthetic congener of paclitaxel. Docetaxel is the first "taxoid," i.e., Taxol-like compound, approved by the FDA for clinical use.

These two first-generation taxane anticancer agents have been clinically used to treat various tumors, including metastatic breast cancer, advanced ovarian cancer, head and neck cancers, non-small cell lung cancer, and Kaposi's sarcoma. Although both paclitaxel and docetaxel possess potent antitumor activity against some tumors, they do not show efficacy against others, such as colon, pancreatic, melanoma, and renal cancers.

In addition, the first generation taxanes are subject to undesirable side effects as well as multi-drug resistance (MDR) upon treatment. The MDR is usually attributed to cells that overexpress P-glycoprotein (Pgp). Pgp is an effective ATP-binding cassette (ABC) transporter which effluxes out hydrophobic anticancer agents, including paclitaxel and docetaxel.

Current cancer chemotherapy is based on the premise that rapidly proliferating tumor cells are more likely to be killed by cytotoxic drugs than healthy cells. However, in reality, the difference in activity of current drugs against tumor tissues compared to healthy tissues is relatively small.

For example, it is well known that representative cytotoxic chemotherapeutic agents like paclitaxel, cisplatin, doxorubicin, and other widely used anticancer drugs cannot distinguish cancer cells from normal dividing cells. Thus, a variety of undesirable side effects associated with these drugs occur in cancer chemotherapy.

Accordingly, a continuing challenge in cancer chemotherapy is to develop new cytotoxic agents with greater selectivity for tumor cells than healthy cells.

It has been shown that particular natural fatty acids are taken up greedily by tumors for use as biochemical precursors and energy sources. These fatty acids include omega-3 fatty acids such as docosahexanoic acid (DHA), eicosapentaenoic acid (EPA), and α-linolenic acid (LNA).

DHA is a constituent of cell membranes and is used as a precursor for metabolic and biochemical pathways. It is also a fatty acid found in human milk, and is classified as a nutritional additive by the United States Food and Drug Administration.

U.S. Pat. Nos. 5,795,909; 5,919,815 and 6,080,877 disclose DHA-conjugated to first generation taxane anticancer agents such as paclitaxel and docetaxel. DHA-paclitaxel conjugates have shown antitumor activity in animal studies. The ability of DHA-paclitaxel conjugates in reducing undesirable side effects is attributed to its selective targeting of the conjugates to tumor cells and use of lower doses compared to unconjugated paclitaxel.

For example, it has been reported (Bradley et al. Clinical Cancer Research (2000) 7, 3229-3238) that DHA-paclitaxel at the optimum dose of 120 mg/kg resulted in complete regression of lung tumor xenografts in a Madison 109 subcutaneous lung tumor model. The regression was sustained for sixty days in all mice. In mice, DHA-paclitaxel exhibits a 74-fold lower volume of distribution and a 94-fold lower clearance rate than paclitaxel. DHA-paclitaxel is stable in plasma, and high concentrations are maintained in mouse plasma for a long period of time. In contrast, paclitaxel at the optimum dose of 20 mg/kg caused neither complete nor partial regression of the tumors in any mice. The conjugate drug appears to be inactive as a cytotoxic agent until metabolized by tumor cells to release palitaxel.

Therefore, DHA-paclitaxel is less toxic than paclitaxel alone. As a result, higher molar doses of the conjugate can be administered. On the basis of the efficacy demonstrated in animal models, DHA-paclitaxel entered human clinical trials, and is currently in Phase III.

Accordingly to the proposed drug-delivery mechanism, DHA-paclitaxel is taken up by tumor cells, internalized, and slowly hydrolyzed by esterases in the cancer cell to release the active cytotoxic agent (e.g., paclitaxel). However, if the cancer cells are overexpressing an active transporter (i.e., "efflux pump"), the paclitaxel molecules, even when released slowly from DHA, will be caught by the efflux pump and eliminated from the cancer cells. Thus, the efficacy of DHA-paclitaxel can be rendered not sufficiently active against drug-resistant cancers.

The structure-activity relationship (SAR) study performed in the inventor's laboratories has shown that the phenyl moieties of paclitaxel at the C-2, C-3', and C-3'N positions are not essential for its potent cytotoxicity and tubulin-binding ability (Ojima et al. *J. Med. Chem.* (1996) 39, 3889-3896). The inventor and his coworkers found that the incorporation of a simpler alkyl or alkenyl substituent at C-3' considerably increased activity against drug-sensitive as well as drug-resistant cancer cell lines. More importantly, appropriate modifications at the C-10 and C-3' positions have led to the development of "second-generation" taxoid anticancer agents. The most significant result with this series of taxoids was their substantially increased potency against drug-sensitive human cancer cell lines as well as remarkable activity against drug-resistant cell lines, expressing MDR phenotypes (e.g., $IC_{50}$=2.1-9.1 nM; paclitaxel $IC_{50}$=300-800 nM against human breast cancer cell line MCF7-MDR). The second-generation taxoids also include a series of taxoids bearing pentacyclic diterpene skeleton derived from 14-hydroxybaccatin III.

Thus, in sharp contrast with paclitaxel and docetaxel, the second-generation taxoids including ortataxel (code names in publications include Bay59-8862, IDN5109 and SB-T-101131), SB-T-1213 and SB-T-121303, exhibit excellent activity against drug-resistant cancer cells expressing MDR phenotypes. For example, ortataxel exhibited impressive activity against human colon carcinoma SW-620 xenografts in mice (Vredenburg et al. *J. Nat'l Cancer Inst.* (2001) 93, 1234-1245).

However, these highly potent second-generation taxoids are not tumor specific. Thus, various undesirable side effects may occur during clinical use.

Accordingly, there is a need for improved anticancer drugs for effectively treating all types of cancer, including multi-drug resistant tumors, while diminishing side effects.

SUMMARY OF THE INVENTION

The above needs have been met by the present invention by providing an improved conjugate. The improved conjugate comprises a second generation taxoid and an omega-3 fatty acid. The improvement relates to the use of a second-generation taxoid.

In another embodiment, the invention provides an improved pharmaceutical composition comprising a conjugate. The conjugate comprises a second-generation taxoid and an omega 3-fatty acid. The improvement relates to the use of a second-generation taxoid.

In yet another embodiment, the invention provides an improved method for treating cancer in a human in need thereof. The method comprises administering an effective amount of a conjugate. The conjugate comprises a second generation taxoid and an omega 3-fatty acid. The improvement relates to the use of a second-generation taxoid.

DETAILED DESCRIPTION OF THE INVENTION

Figure 1:
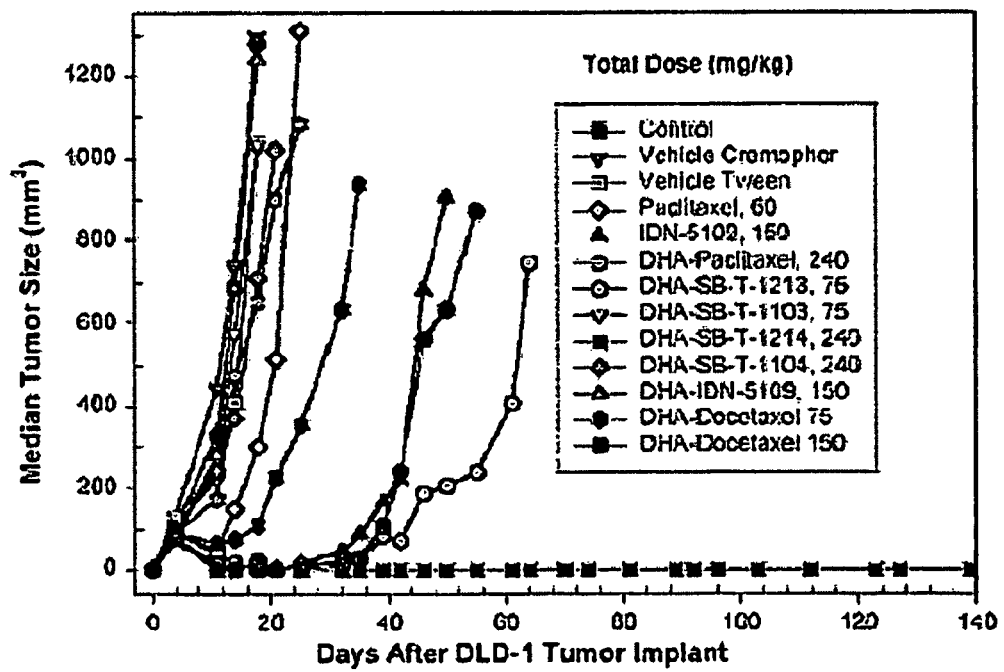
FIG. 1. Effect of DHA-Taxoid Conjugates on Human Colon Tumor Xenograft (pgp+) DLD-1.

The present invention relates to improved conjugates of taxoids and omega-3 fatty acids. Taxoids useful in the present invention are second-generation taxoids of the general formula I, wherein FA is an omega-3 fatty acid residue;

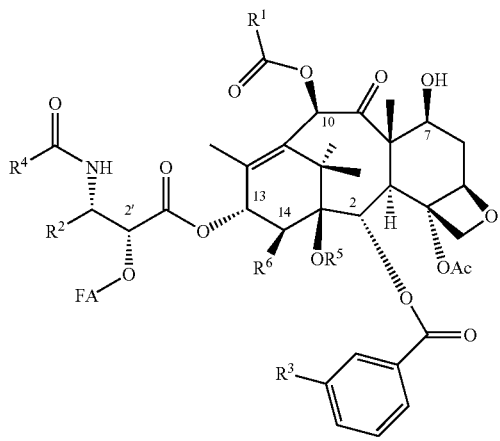

Formula I $R^1$ represents C1-C6 alkyl or alkenyl, dialklylamino or alkylamino, or alkoxy,
$R^2$ represents $C_3$-$C_5$ alkyl or alkenyl or trifluoromethyl;
$R^3$ represents H, methyl, methoxy, chloro, fluoro or azido;
$R^4$ represents C3-C6 cycloalkyl or cycloakenyl or an alkoxy;
$R^5$ and $R^6$ are both hydrogens or $R^5$ and $R^6$ together represent oxycarbonyl, forming thereby a cyclic carbonate (see formula II).

Examples of second-generation taxoids include ortataxel, SB-T-1103, SB-T-11033, SB-T-1104, SB-T-11043, SB-T-1107, SB-T-11073, SB-T-1213, SB-T-121303, SB-T-1214, SB-T-121403, SB-T-1216, SB-T-121603, SB-T-1217, SB-T-121703, SB-T-12821, and SB-T-128221-3, whose structures are shown below (see formula II and III):

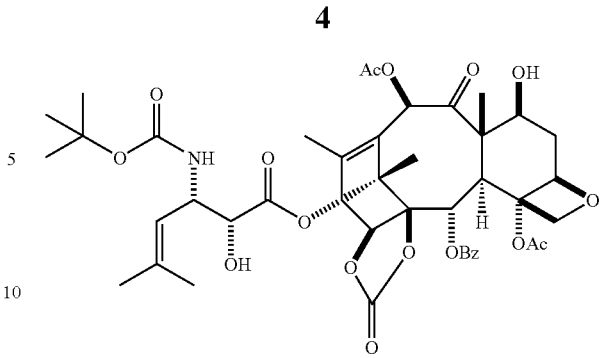

Formula II: Ortataxel (Bay59-8862; IDN5109; SB-T-101131)

Formula III

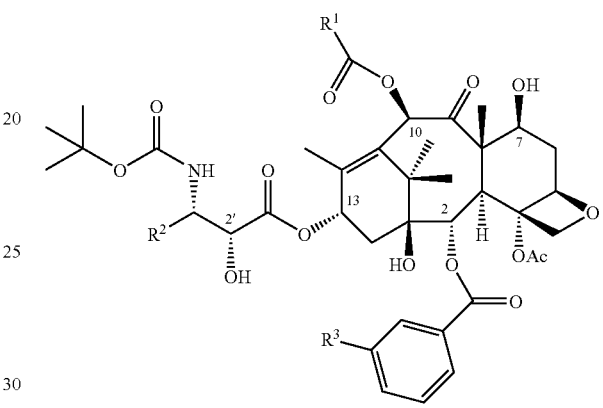

SB-T-1103: $R^1 = C_2H_5$, $R^2 =$ 2-methylpropyl; $R^3 =$ H
SB-T-11033: $R^1 = C_2H_5$, $R^2 =$ 2-methylpropyl; $R^3 = CH_3O$
SB-T-1104: $R^1 =$ cyclopropyl, $R^2 =$ 2-methylpropyl; $R^3 =$ H
SB-T-11043: $R^1 =$ cyclopropyl, $R^2 =$ 2-methylpropyl; $R^3 = CH_3O$
SB-T-1107: $R^1 = CH_3O$, $R^2 =$ 2-methylpropyl; $R^3 =$ H
SB-T-11073: $R^1 = CH_3O$, $R^2 =$ 2-methylpropyl; $R^3 = CH_3O$
SB-T-1213: $R^1 = C_2H_5$, $R^2 =$ 2-methyl-1-propenyl; $R^3 =$ H
SB-T-121303: $R^1 = C_2H_5$, $R^2 =$ 2-methyl-1-propenyl; $R^3 = CH_3O$
SB-T-1214: $R^1 =$ cyclopropyl, $R^2 =$ 2-methyl-1-propenyl; $R^3 =$ H
SB-T-121403: $R^1 =$ cyclopropyl, $R^2 =$ 2-methyl-1-propenyl; $R^3 = CH_3O$
SB-T-1216: $R^1 = (CH_3)_2N$, $R^2 =$ 2-methyl-1-propenyl; $R^3 =$ H
SB-T-121603: $R^1 = (CH_3)_2N$, $R^2 =$ 2-methyl-1-propenyl; $R^3 = CH_3O$
SB-T-1217: $R^1 = CH_3O$, $R^2 =$ 2-methyl-1-propenyl; $R^3 =$ H
SB-T-121703: $R^1 = CH_3O$, $R^2 =$ 2-methyl-1-propenyl; $R^3 = CH_3O$
SB-T-12821: $R^1 = (CH_3)_2N$, $R^2 =$ trifluoromethyl; $R^3 =$ H
SB-T-128221-3: $R^1 = C_2H_5$, $R^2 =$ trifluoromethyl; $R^3 = CH_3O$ The syntheses and structures of second-generation taxoids useful in the present invention are disclosed by Ojima et al. in their publications (*Bioorg. Med. Chem. Lett.* (1999) 9, 3423-3428; *J. Med. Chem.* (1996) 39, 3889-3896; *J. Med. Chem.* (1997) 40, 267-278; *Bioorg. Med. Chem. Lett.*, (1997) 7, 133-138) and U.S. Pat. Nos. 6,096,909; 6,100,411; 6,458,976 and 6,500,858. The synthesis and structures disclosed in the articles and patents mentioned above are hereby incorporated by reference. For example, the syntheses and structures of compounds 7a-7q listed in Table I of the publication by Ojima et al. (*Bioorg. Med. Chem. Lett.* (1999) 9, 3423-3428); compounds 1a-1s, 3a-3s and 4a-4s listed in Table 2; compounds 5a-5e and 5s listed in Table 3 of the publication by Ojima et al. (*J. Med. Chem.* (1996) 39, 3889-3896); compounds 7a-7i listed in Table 2 of the publication by Ojima et al. (*Bioorg. Med. Chem. Lett.*, (1997) 7, 133-138), and compounds 17b-17g, 22b, 22d, and 22e listed in Table 6 of the publication by Ojima et al. (*J. Med. Chem.* (1997) 40, 267-278) are incorporated by reference.

A second-generation taxoid is conjugated to an omega-3 fatty acid. Any omega-3 fatty acid can be used in accordance with the present invention. Examples of omega-3 fatty acids include docosahexaenoic acid (DHA), eicosapentaenoic acid (EPA), and α-linolenic acid (LNA). The structures of these fatty acids are shown below (see formula IV, V and VI):

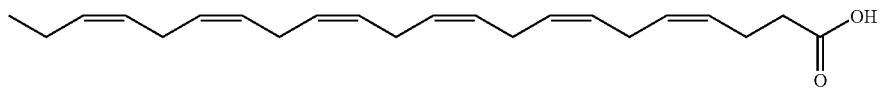

Formula IV: Docosahexaenoic acid (DHA)

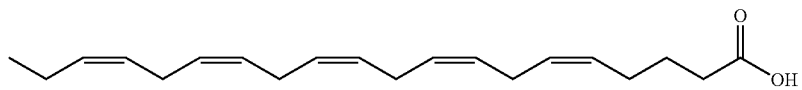

Formula V: Eicosapentaenoic acid (EPA)

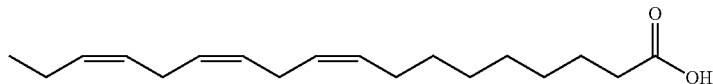

Formula VI: α-Linolenic acid (LNA)

DHA can be isolated, for example, from fish oil, or can be chemically synthesized. Preferably, DHA is produced by biological synthesis, such as by the methods disclosed in U.S. Pat. Nos. 5,374,657; 5,492,938; 5,407,957 and 5,397,591, the specifications of which are hereby incorporated by reference. DHA can also be purchased from, for example, Martek Biosciences Corporation, Columbia, Md.

EPA can be isolated from, for example, marine oils (i.e., fish and shellfish). Marine oils are produced from the body of fatty fish, livers of lean fish, as well as from blubber of marine mammals, such as whales and seals. Commercial fish oils include inter alia the oils of anchovy (*Engraulis* spp.), capelin (*Mallotus* spp.), cod and cod liver (*Gadus* spp.), herring (*Cupea* spp.), horse mackerel (*Scomber* spp.), tuna (*Euthynnus* spp.), menhaden (*Brevoortia* spp.), salmon (*Salmo salar*, syn. *Oncorhynchus* spp.), rainbow trout (*Oncorhynchus mykiss*), and sardine (*Sardina* spp.). Marine oils form a significant proportion (2-3%) of the world's edible oil production. The relative amount of EPA and DHA varies from 5-20 and 3-26% of fatty acids.

Alternatively, EPA can be synthesized by any method known in the art. For instance, EPA can be synthesized through desaturation and elongation of dietary LNA (A. Kamal-Eldin and N. V. Yanishlieva, Eur. J. Lipid Sci. Technol. (2002), 104, 825-836). EPA can also be commercially obtained from, for example, Sigma-Aldrich Chemicals Co. (St. Louis, Mo.).

Major sources of LNA include the seeds and oils of flaxseed (*Linum usitatissimum*), perilla (*Perilla frutescens*), soybean (*Glycine max*), rapeseed/canola (*Brassica* spp.), and walnut (*Juglans regia*) (R. A. Riemersma, Eur. J. Lipid Sci. Technol. (2001) 103, 372-373; A. Kamal-Eldin and R. Andersson, J. Am. Oil Chem. Soc. (1997) 74, 375-380; G. P. Savage, P. C. Dutta, and D. L. McNeil, J. Am. Oil Chem. Soc. (1999) 76, 1059-1063). Other nuts, peas, beans, and green leafy vegetables also provide considerable amounts of dietary LNA (M. A. Allman, Food Australia (1995) 47, S14-S17; P. J. Ghafoorunissa, J. Agric. Food Chem. (1993) 47, 121-124). LNA can be obtained commercially from, for example, Sigma-Aldrich Chemicals Co.

A second-generation taxoid-omega-3 fatty acid conjugate can be prepared by coupling an omega-3 fatty acid to a second-generation taxoid by any method known to those in the art. For example, an omega-3 fatty acid can be coupled to either the C-2' hydroxyl group or the C-7 hydroxyl group of a second-generation taxoid. Preferably, the omega-3 fatty acid is coupled to the C-2' position of a second-generation taxoid.

The coupling reaction can occur in one or more steps. For example, selective coupling of an omega-3 fatty acid to the C-2' hydroxyl of a second-generation taxoid can be achieved in a single step by using any dehydrating agent known to those in the art. Examples of suitable dehydrating agents include dicyclohexylcarbodiimide (DCC) and diisopropylcarbodiimide (DIC). The dehydrating agent can be used in the presence or absence of an amine base such as, for instance, 4-N,N-dimethylaminopyridine (DMAP).

A general scheme for preparing omega-3 fatty acid-taxoid conjugates is shown below. In this scheme, DHA is used as the omega-3 fatty acid. Other omega-3 fatty acids, such as those described above, can be coupled to the C-2' hydroxyl group of a taxoid in the same manner.

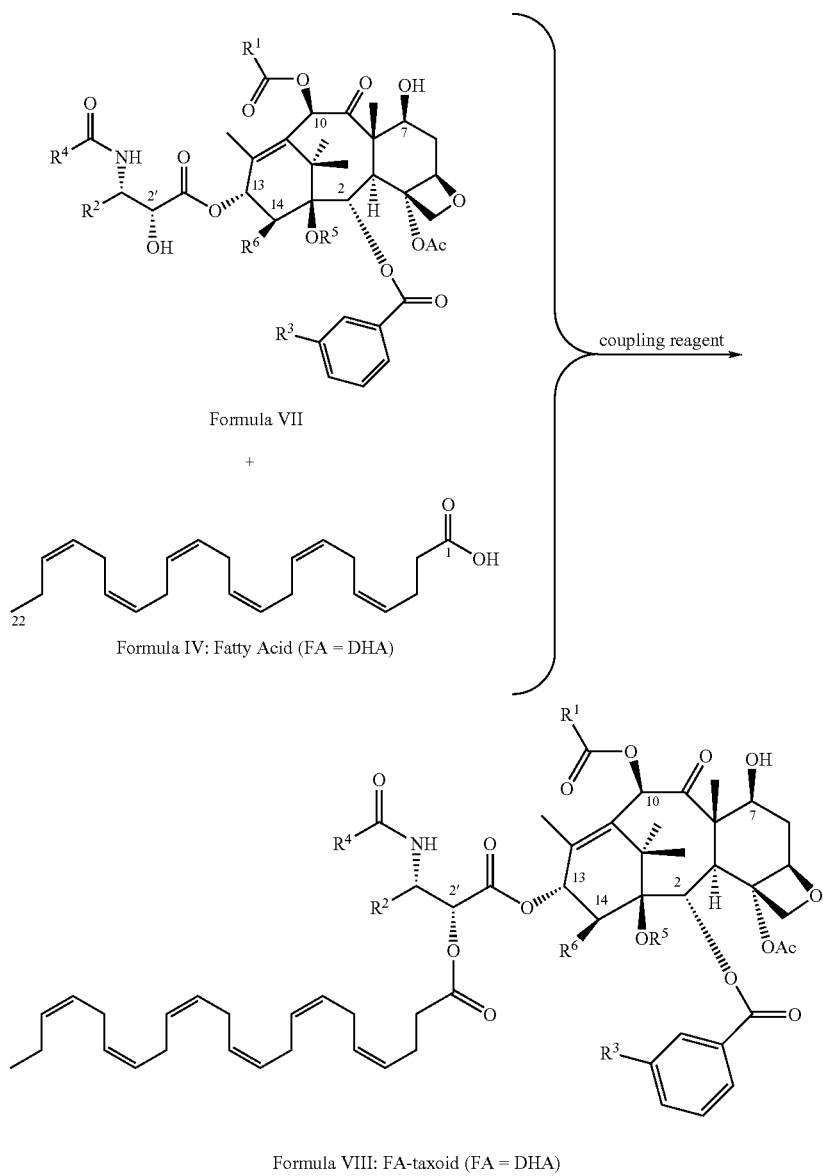

Formula VII

Formula IV: Fatty Acid (FA = DHA)

Formula VIII: FA-taxoid (FA = DHA)

Omega-3 fatty acids can be unstable in the presence of oxygen. Measures can be taken to stabilize the second-generation taxoid-fatty acid conjugates. For example, anti-oxidants can be added to the conjugates after synthesis. Examples of suitable anti-oxidants include, but are not limited to, ascorbic acid, ascorbyl palmitate, dilauryl ascorbate, hydroquinone, butylated hydroxyanisole, sodium meta bisulfite, t-β-carotene and α-tocopherol. Heavy metal cheloators, such as ethylenediamine tetraacetic acid (EDTA) can also be used.

The second-generation taxoid-fatty acid conjugates of the present invention are useful for treating cancer in a human in need thereof. The cancer can be any type of cancer that is sensitive to the second-generation taxoids. Examples of cancers include breast, ovary, lung, head and neck, colon, pancreatic, melanoma, brain, prostate and renal cancer.

The method of the invention comprises administering an effective amount of a second-generation taxoid-fatty acid conjugate. An effective amount of a second-generation taxoid-fatty acid conjugate is any amount effective in treating the cancer.

The actual amounts of the second-generation taxoid-fatty acid conjugate for a specific case will vary according to various factors that are well known to those in the art, such as the type of cancer, the particular second-generation taxoid-fatty acid conjugate utilized, the mode of administration, and the particular subject treated. The effective amount can be determined during pre-clinical trials and clinical trials by methods familiar to physicians and clinicians.

The minimal amount of a second-generation taxoid-fatty acid conjugate administered to a human is the lowest amount capable of treating the cancer. The maximum amount is the highest effective amount that does not cause undesirable side effects. Generally, daily oral doses of the second-generation taxoid-fatty acid conjugate can be from about 0.01 mg/kg per day to 1000 mg/kg per day. Usually systemic doses in the range of about 1 to 1000 mg/m² per day can be administered. Higher doses may be employed to treat the cancer to the extent patient tolerance permits.

The second-generation taxoid-fatty acid conjugate may be administered by any appropriate method known in the art. Some examples of modes of administration include oral and systemic administration. Typically, the conjugates of the present invention are administered systemically. Systemic administration can be enteral or parenteral.

Parenteral administration of the second-generation taxoid-fatty acid conjugate include, for example intravenous, intramuscular, and subcutaneous injections or infusions. For instance, a second-generation taxoid-fatty acid conjugate may be administered to a patient by sustained release, as is known in the art. Sustained release administration is a method of drug delivery to achieve a certain level of the drug over a particular period of time.

Other routes of administration include oral, topical, intrabronchial, or intranasal administration. For oral administration liquid or solid formulations may be used. Some examples of formulations suitable for oral administration include tablets, gelatin capsules, pills, troches, elixirs, suspensions, syrups, and wafers. Intrabronchial administration can include an inhaler spray. For intranasal administration, administration of a second-generation fatty acid conjugate can be accomplished by a nebulizer or liquid mist.

The invention further comprises a second-generation fatty acid conjugate in a suitable pharmaceutical carrier. In this specification, a pharmaceutical carrier is considered to be synonymous with a vehicle as is understood by practitioners in the art. Examples of carriers include magnesium or calcium stearate, talc, vegetable fats or oils, gums and glycols.

The second-generation taxoid-fatty acid conjugate may also comprise one or more of a stabilizer, a surfactant, preferably a nonionic surfactant, and optionally a salt and/or a buffering agent.

The stabilizer may, for example, be an amino acid, such as for instance, glycine; or an oligosaccharide, such as for example, sucrose, tetralose, lactose or a dextran. Alternatively, the stabilizer may be a sugar alcohol, such as for instance, mannitol; or a combination thereof. Preferably the stabilizer or combination of stabilizers constitutes from about 0.1% to about 10% weight for weight of the second-generation fatty acid conjugate.

The surfactant is preferably a nonionic surfactant, such as a polysorbate. Some examples of suitable surfactants include Tween 20, Tween 80; a polyethylene glycol or a polyoxyethylene polyoxypropylene glycol, such as Pluronic F-68 at from about 0.001% (w/v) to about 10% (w/v).

The salt or buffering agent may be any salt or buffering agent, such as for example sodium chloride, or sodium/potassium phosphate, respectively. Preferably, the buffering agent maintains the pH of the second-generation fatty acid conjugate in the range of about 5 to about 8. The salt and/or buffering agent is also useful to maintain the osmolality at a level suitable for administration to a human. Preferably the salt or buffering agent is present at a roughly isotonic concentration of about 150 mM to about 300 mM.

The second-generation fatty acid conjugate may additionally contain one or more conventional additives. Some examples of such additives include a solubilizer such as, for example, glycerol; an antioxidant such as for example, benzalkonium chloride (a mixture of quaternary ammonium compounds, known as "quart"), benzyl alcohol, chloretone or chlorobutanol; anaesthetic agent such as for example a morphine derivative; or an isotonic agent etc., such as described above. As a further precaution against oxidation or other spoilage, the second-generation fatty acid conjugate may be stored under nitrogen gas in vials sealed with impermeable stoppers.

The following non-limiting examples are illustrative of the present invention. It should be noted that various changes would be made in the above examples and processes therein without departing from the scope of the present invention. For this reason, it is intended that the illustrative embodiments of the present application should be interpreted as being illustrative and not limiting in any sense.

EXAMPLE 1

2'-Docosahexaenoyl 3'-dephenyl-3'-(2-methyl-2-propyl)-10-(methoxycarbonyl)docetaxel (DHA-SB-T-1107)

To a solution of 3'-dephenyl-10-(methoxycarbonyl)-3'-(2-methyl-2-propyl)-2'-docosahexaenoyl-docetaxel (SB-T-1107) (63.9 mg, 75 µmol) in dichloromethane (3.5 mL) under argon were added 4-dimethylaminopyridine (9 mg; 75 µmol), 1,3-dicyclohexylcarbodiimide (19 mg; 150 µmol), and DHA (27 mg; 83 µmol). The reaction mixture was stirred at ambient temperature for 1 h. After dilution with dichloromethane, the reaction mixture was washed with 5% hydrochloric acid, water, and brine. The organic layer was dried over anhydrous magnesium sulfate and concentrated in vacuo. The crude product was purified by chromatography on silica gel (ethyl acetate/hexanes=1/3 to 1/1) to give 78.5 mg (90% yield) of DHA-SB-T-1107 as white solid: m.p. 102-105° C., $[\alpha]_D^{22}$ −45.0 (c 1.0, CHCl$_3$); $^1$H NMR (400 MHz, CDCl$_3$) δ 0.96 (m, 9 H), 1.14 (s, 3H), 1.22 (s, 3H), 1.30 (s, 9H), 1.67 (m, 3H), 1.69 (s, 3H), 1.88 (m, 1H), 1.96 (s, 3H), 2.07 (m, 2H), 2.37 (s, 3H), 2.47 (m, 6H), 2.55 (m, 1H), 2.85 (m, 10 H), 3.78 (d, J=6.8 Hz, 1H), 3.86 (s, 3H), 4.19 (d, J=8.2 Hz, 1H), 4.29 (d, J=8.2 Hz, 1H), 4.37 (m, 1H), 4.43 (m, 1H), 4.60 (d, J=9.3 Hz, 2H), 4.91 (s, 1H), 4.97 (d, J=8.0 Hz, 1H), 5.25-5.50 (m, 12H), 5.66 (d, J=7.0 Hz, 1H), 6.12 (s, 1H), 6.20 (t, J=8.8 Hz, 1H), 7.47 (t, J=8.0 Hz, 2H), 7.59 (t, J=8.0 Hz, 1H), 8.11 (d, J=8.0 Hz, 2H); $^{13}$C NMR (CDCl$_3$, 400 MHz) δ 9.6, 14.3, 20.6, 21.9, 22.1, 22.5, 22.6, 23.2, 24.7, 25.6, 25.7, 25.7, 25.8, 26.6, 28.2, 33.7, 35.5, 35.6, 41.4, 43.1, 45.6, 48.9, 55.5, 58.5, 71.5, 72.0, 74.4, 75.1, 76.4, 76.9, 78.3, 79.2, 79.7, 80.9, 84.4, 126.9, 127.4, 127.7, 127.8, 127.9, 128.3, 128.3, 128.4, 128.5, 128.7, 129.2, 129.5, 130.1, 130.2, 130.2, 131.9, 133.4, 144.2, 155.1, 155.6, 166.8, 168.1, 169.4, 172.1, 203.9.

EXAMPLES 2-9

Other DHA-taxoids were synthesized in the same manner as described for the synthesis of DHA-SB-T-1107 in EXAMPLE 1. Characterization data for these DHA-taxoids are shown below.

EXAMPLE 2

2'-Docosahexaenoyl-3'-dephenyl-3'-(2-methylpropyl)-10-propanoyldocetaxel (DHA-SB-T-1103)

75% yield; white solid; m.p. 94-98° C., $[\alpha]_D^{22}$ −37.9 (c 1.08, CHCl$_3$); $^1$H NMR (400 MHz, CDCl$_3$) δ 0.97 (m, 9H), 1.13 (s, 3H), 1.22-1.27 (m, 6H), 1.31 (s, 9H), 1.56 (s, 3H), 1.67 (s, 3H), 1.90 (m, 1H), 1.94 (s, 3H), 2.08 (m, 2H), 2.39 (s, 3H), 2.40 (m, 2H), 2.46-2.60 (m, 7H), 2.85 (m, 10H), 3.82 (d, J=7.0 Hz, 1H), 4.20 (d, J=8.4 Hz, 1H), 4.30 (d, J=8.4 Hz, 1H), 4.35 (m, 1 H), 4.46 (dd, J=10.2, 6.7 Hz, 1H), 4.60 (d, J=10.4 Hz, 1H), 4.92 (d, J=2.4 Hz, 1H), 4.98 (d, J=7.6 Hz, 1H), 5.40

(m, 12H), 5.67 (d, J=7.6 Hz, 1H), 6.23 (m, 1H), 6.31 (s, 1H), 7.48 (t, J=7.6 Hz, 2H), 7.60 (t, J=7.6 Hz, 1H), 8.12 (d, J=7.6 Hz, 2H); $^{13}$C NMR (400 MHz, CDCl$_3$) δ 9.0, 9.6, 14.1, 14.3, 14.8, 20.5, 21.9, 22.2, 22.4, 22.5, 22.6, 23.2, 24.5, 25.5, 25.6, 26.6, 27.5, 28.1, 28.3, 33.7, 35.5, 41.3, 43.2, 45.6, 48.9, 58.8, 71.5, 72.2, 74.4, 75.2, 75.5, 76.4, 77.3, 79.3, 79.8, 81.0, 84.4, 127.0, 127.5, 127.8, 127.9, 128.0, 128.3, 128.4, 128.5, 128.6, 129.3, 129.6, 130.2, 132.0, 132.4, 133.5, 143.4, 155.3, 167.0, 168.4, 169.6, 172.3, 174.6, 204.0.

EXAMPLE 3

2'-Docosahexaenoyl-3'-dephenyl-3'-(2-methyl-1-propenyl)-10-cyclopropanecarbonyldocetaxel (DHA-SB-T-1214)

69% yield; white solid; m.p. 64-67° C., $[α]_D^{22}$ −52.2 (c 1.8, CHCl$_3$); $^1$H NMR (CDCl$_3$) δ 0.99 (t, J=7.5 Hz, 3H), 1.15 (m, 4H), 1.28 (s, 3H), 1.36 (s, 9H), 1.68 (s, 3H), 1.75 (m, 1H), 1.78 (s, 6 H), 1.93 (m, 1H), 1.95 (s, 3H), 2.09 (q, J=7.5, 15.0 Hz, 2H), 2.39 (s, 3H), 2.48 (m, 2H), 2.56 (m, 2H), 2.65 (d, J=3.9 Hz, 1H), 2.87 (m, 10H), 3.83 (d, J=6.9 Hz, 1H), 4.20 (d, J=8.7 Hz, 1H), 4.33 (d, J=8.1 Hz, 1H), 4.46 (m, 1H), 4.82 (d, J=8.8 Hz, 1H), 4.95 (s, 1H), 4.99 (d, J=9.3 Hz, 1H), 5.21 (d, J=7.8 Hz, 1H), 5.41 (m, 12H), 5.69 (d, J=7.2 Hz, 1H), 6.21 (t, J=8.8 Hz, 1H), 6.32 (s, 1H), 7.50 (t, J=8.1 Hz, 2H), 7.63 (t, J=7.5 Hz, 1H), 8.13 (d, J=7.2 Hz, 2 H); $^{13}$C NMR (CDCl$_3$) δ 9.14, 9.36, 9.47, 9.53, 12.98, 14.25, 14.76, 14.81, 18.48, 18.54, 20.52, 22.22, 22.39, 22.47, 25.59, 25.74, 26.67, 28.13, 28.18, 29.67, 33.62, 35.42, 43.12, 45.52, 45.58, 48.86, 58.42, 71.70, 72.17, 74.45, 74.57, 75.19, 75.38, 75.44, 76.35, 79.25, 79.86, 80.92, 84.40, 84.52, 119.95, 127.50, 127.84, 128.02, 128.26, 128.60, 129.21, 129.58, 130.14, 132.40, 133.59, 137.94, 143.48, 154.85, 166.96, 168.30, 169.61, 172.29, 175.12, 204.10.

EXAMPLE 4

2'-Docosahexaenoyl-3'-dephenyl-3'-(2-methyl-1-propyl)-10-cyclopropanecarbonyldocetaxel (DHA-SB-T-1104)

73% yield; white solid; m.p. 65-68° C.; $[α]_D$ −53.4 (c 2.5, CHCl$_3$); $^1$H NMR (CDCl$_3$) δ0.99 (m, 9H), 1.15 (m, 6H), 1.27 (s, 3H), 1.33 (s, 9H), 1.69 (s, 6H), 1.78 (m, 1H), 1.95 (s, 3H), 2.09 (q, J=7.2, 14.7 Hz, 2H), 2.43 (s, 3H), 2.48 (m, 2H), 2.56 (m, 2H), 2.65 (d, J=3.6 Hz, 2H), 2.87 (m, 10H), 3.83 (d, J=7.2 Hz, 1H), 4.21 (d, J=8.1 Hz, 1H), 4.32 (d, J=8.1 Hz, 1H), 4.46 (m, 1H), 4.63 (d, J=10.2 Hz, 1H), 4.93 (d, J=2.1 Hz, 1H), 4.99 (d, J=8.1 Hz, 1H), 5.41 (m, 12H), 5.68 (d, J=6.9 Hz, 1H), 6.23 (t, J=8.7 Hz, 1H), 6.31 (s, 1H), 7.50 (t, J=8.1 Hz, 2H), 7.63 (t, J=7.5 Hz, 1H), 8.13 (d, J=7.2 Hz, 2H); $^{13}$C NMR (CDCl$_3$) δ 3.9, 4.1, 4.3, 7.8, 9.0, 9.6, 15.3, 16.6, 17.0, 17.1, 17.3, 17.5, 18.0, 19.4, 20.2, 20.3, 20.4, 21.4, 22.8, 22.9, 28.4, 36.0, 36.1, 37.9, 40.4, 43.6, 53.2, 67.0, 69.2, 70.0, 70.2, 70.9, 70.95, 71.1, 71.15, 71.2, 71.7, 72.2, 74.1, 74.6, 75.7, 79.2, 92.8, 121.8, 122.3, 122.6, 122.7, 122.8, 123.1, 123.15, 123.2, 123.4, 123.45, 124.1, 124.4, 125.0, 126.8, 127.2, 127.25, 128.3, 138.3, 150.1, 161.8, 163.2, 164.4, 167.1, 169.9, 198.9.

EXAMPLE 5

2'-Docosahexaenoyl-3'-dephenyl-3'-(2-methyl-1-propenyl)-10-propanoyldocetaxel (DHA-SB-T-1213)

72% yield; white solid; m.p. 67-69° C.; $[α]_D^{22}$ −72.7 (c 0.73, CHCl$_3$); $^1$H NMR (CDCl$_3$) δ 0.99 (t, J=7.5 Hz, 3H), 1.16 (s, 3H), 1.27 (m, 8H), 1.28 (s, 3H), 1.36 (s, 9H), 1.68 (s, 3H), 1.75 (m, 1 H), 1.78 (s, 9H), 1.93 (m, 1H), 1.95 (s, 3H), 2.09 (q, J=7.5, 15.0 Hz, 2H), 2.40 (s, 3H), 2.46 (m, 3H), 2.53 (m, 2H), 2.56 (m, 2H), 2.65 (d, J=3.9 Hz, 2H), 2.87 (m, 10H), 3.84 (d, J=6.9 Hz, 1H), 4.20 (d, J=8.4 Hz, 1H), 4.33 (d, J=8.4 Hz, 1H), 4.48 (m, 1H), 4.82 (d, J=8.8 Hz, 1H), 4.93 (s, 1H), 4.99 (d, J=9.6 Hz, 1H), 5.21 (d, J=7.8 Hz, 1H), 5.41 (m, 12H), 5.69 (d, J=6.9 Hz, 1H), 6.21 (t, J=8.8 Hz, 1H), 6.33 (s, 1H), 7.50 (t, J=8.1 Hz, 2H), 7.63 (t, J=7.5 Hz, 1H), 8.13 (d, J=7.2 Hz, 2H); $^{13}$C NMR (CDCl$_3$) δ 9.28, 9.79, 9.86, 14.53, 15.00, 15.06, 18.76, 18.83, 20.81, 22.35, 22.68, 22.76, 25.87, 26.83, 27.80, 28.41, 28.47, 29.94, 33.91, 35.72, 43.42, 45.90, 49.15, 58.70, 71.98, 72.37, 74.74, 75.42, 75.68, 75.75, 76.64, 79.50, 80.16, 81.19, 84.67, 84.80, 127.78, 128.11, 128.30, 128.59, 128.90, 129.50, 129.86, 130.42, 132.71, 133.89, 138.24, 143.56, 155.17, 167.24, 168.60, 169.92, 172.60, 174.90, 204.28.

EXAMPLE 6

2'-Docosahexaenoyl-3'-dephenyl-3'-(2-methylpropyl)-10-acetyldocetaxel-1,14-carbonate (DHA-Ortataxel)

68% yield; white solid; m.p. 72-75° C.; $[α]_D^{22}$ −40 (c 0.6, CHCl$_3$); $^1$H NMR (CDCl$_3$) δ 0.99 (t, 3 H), 1.00 (m, 3H), 1.25 (s, 3H), 1.28 (s, 3H), 1.36 (s, 9H), 1.36-1.47 (m, 2H), 1.63-1.70 (m, 2 H), 1.72 (s, 3H), 1.90 (d, 3H), 2.07 (m, 2H), 2.25 (s, 3H), 2.35 (s, 1H), 2.47 (m, 4H) 2.49 (s, 3 H), 2.50-2.62 (m, 2H), 2.83 (m, 10H), 3.71 (d, 1H), 4.20-4.30 (m, 2H), 4.38-4.44 (m, 2H), 4.57-4.62 (d, 2H), 4.850 (d, 1H), 4.951 (d, 1H), 5.09 (d, 1H), 5.40 (m, 12H), 6.11 (d, 1H), 6.27 (s, 1H), 6.44 (d, 1H), 7.49 (t, 2H), 7.61 (t, 1H), 8.03 (d, 2H); $^{13}$C NMR (CDCl$_3$) δ 9.68, 14.10, 14.20, 15.0, 20.5, 20.6, 22.0, 22.5, 22.6, 23.1, 23.4, 23.4, 24.7, 25.5, 25.6, 25.9, 28.2, 28.2, 29.7, 33.9, 35.4, 41.7, 45.0, 58.7, 69.5, 71.7, 74.3, 74.4, 74.8, 75.9, 79.5, 80.1, 80.5, 84.2, 88.1, 127.0, 127.4, 127.8, 128.0, 128.3, 128.4, 128.6, 128.9, 129.7, 129.9, 132.0, 133.3, 134.0, 140.5, 151.8, 155.1, 164.8, 167.8, 170.2, 170.8, 172.3, 202.3.

EXAMPLE 7

2'-Docosahexaenoyl-3'-dephenyl-3'-(2-methyl-2-propyl)-2-debenzoyl-2-(3-methoxybenzoyl)-10-(methoxycarbonyl)docetaxel (SB-T-110703-DHA)

62% yield; white solid; $^1$H-NMR (CDCl$_3$, 300 MHz): δ 7.74 (d, 1H, J=7.5 Hz), 7.67 (d, 1H, J=1.2 Hz), 7.39 (dd, 1H, J=8.1 Hz), 7.16 (dd, 1H, J=2.7 Hz, J=8.1 Hz), 6.24 (dd, 1H, J=8.7 Hz), 6.14 (s, 1H), 5.686 (d, 1H, J=7.2 Hz), 5.62-5.24 (m, 12H), 5.03-4.98 (m, 1H), 4.93 (d, 1H, J=2.4 Hz), 4.63 (d, 1H, J=10.5), 4.48-4.29 (m, 3H), 4.21 (d, 1H, J=8.1 Hz), 3.9 (s, 3H), 3.88 (s, 3H), 3.81 (d, 1H, J=6.9 Hz), 2.91-2.78 (m, 10H), 2.65-2.22 (m, 11H), 2.19-2.06 (m 2H), 1.98 (s, 3H), 1.97-1.82 (m, 1H), 1.4-1.1 (m, 15H), 1.02-0.94 (m, 9H); $^{13}$C-NMR (CDCl$_3$, 75.5 MHz): δ 9.8, 14.5, 15.1, 20.8, 21.9, 22.3, 22.8, 23.5, 23.7, 24.9, 25.8, 25.9, 26.8, 28.3, 33.9, 35.6, 35.8, 41.5, 43.3, 45.8, 49.0, 55.8, 58.7, 71.7, 72.3, 74.8, 75.4, 76.6, 78.6, 79.5, 80.1, 81.2, 84.7, 114.2, 120.9, 123.3, 127.3, 127.8, 128.1, 128.2, 128.3, 128.6, 128.7, 128.8, 129.9, 130.7, 132.3, 144.6, 155.5, 156.1, 159.9, 167.1, 168.6, 169.9, 172.6, 204.5.

EXAMPLE 8

2'-Docosahexaenoyl-3'-dephenyl-3'-(2-methyl-2-propenyl)-2-debenzoyl-2-(3-methoxybenzoyl)-10-propanoyldocetaxel (DHA-SB-T-121303)

67% yield; white solid; $^1$H NMR (CDCl$_3$) δ 0.99 (t, J=7.5, 3H), 1.14 (s, 3H), 1.28 (m, 8H), 1.33 (s, 9H), 1.66 (m, 3H), 1.73 (s, 3H), 1.75 (s, 3H), 1.89 (m, 5H), 2.10 (m, 2H), 2.37 (m, 6 H), 2.53 (m, 7H), 2.87 (m, 10H), 3.80 (d, J=6.9 Hz, 1H), 3.86 (s, 3H), 4.12 (d, J=8.5 Hz, 1 H), 4.31 (d, J=8.5 Hz, 1H), 4.40 (dd, J=10.6, 6.8 Hz, 1H), 4.72 (m, 2H), 4.95 (m, 2H), 5.30 (d, J=7.6 Hz, 1H), 5.41 (m, 12H), 5.65 (d, J=7.0 Hz, 1H), 6.16 (t, J=8.6 Hz, 1H), 6.30 (s, 1 H), 7.13 (d, J=7.9 Hz, 1H), 7.33 (t, J=8.0 Hz, 1H), 7.62 (s, 1H), 7.69 (d, J=7.6 Hz, 1H).

EXAMPLE 9

2'-Docosahexaenoyl-3'-dephenyl-3'-(2-methyl-2-propyl)-2-debenzoyl-2-(3-methoxybenzoyl)-10-propanoyldocetaxel (DHA-SB-T-11033)

81% yield; m.p. 68-70° C.; $^1$H NMR (CDCl$_3$) δ 1.00 (m, 9H) 1.28 (m, 9 H), 1.36 (s, 9H), 1.73 (s, 3H), 1.91 (m, 1H), 1.99 (s, 3H), 2.15 (m, 2H), 2.40-2.70 (m, 12H), 2.91 (m, 10H) 3.89 (d, J=7 Hz, 1H), 3.95 (s, 3H), 4.24 (d, J=8 Hz, 1H), 4.40 (m, 2H), 4.52 (m, 1H), 4.66 (d, J=10 Hz, 1H), 4.97 (bd, J=1.8 Hz, 1H), 5.00 (bd, J=8 Hz, 1H), 5.45 (m, 12H), 5.73 (d, J=7 Hz, 1H), 6.28 (m, 1H), 6.37 (s, 1H), 7.20 (m, 1H), 7.40 (m, 1H), 7.70 (m, 1H), 7.80 (m, 1H); $^{13}$C NMR (CDCl$_3$) δ 9.3, 9.9, 14.6, 15.0, 20.8, 22.0, 22.5, 22.8, 23.5, 24.9, 25.8, 25.9, 26.9, 27.8, 28.4, 33.9, 35.7, 41.6, 43.4, 45.8, 49.1, 55.6, 58.7, 71.7, 72.5, 74.8, 75.5, 75.7, 76.7, 79.5, 80.1, 81.4, 84.7, 127.3, 127.8, 128.1, 128.2, 128.3, 128.6, 128.7, 128.9, 129.9, 130.7, 132.3, 132.7, 143.6, 155.6, 167.1, 168.7, 169.9, 172.6, 174.9, 204.3.

EXAMPLES 10-12

α-Linolenic acid-taxoids were synthesized in the same manner as described for the synthesis of DHA-SB-T-1107 in EXAMPLE 1. Characterization data for these α-linolenic acid-taxoids are shown below.

EXAMPLE 10

2'-Linolenoyl-3'-dephenyl-3'-(2-methyl-1-propenyl)-10-propanoyldocetaxel (LNA-SB-T-1213)

42% yield; white solid; $^1$H NMR (400 MHz, CDCl$_3$) δ 0.99 (t, J=7.65 Hz, 3H), 1.15 (s, 3H), 1.23 (s, 3H), 1.25 (s, 3H), 1.25-1.35 (m, 12H), 1.34 (s, 9H), 1.67 (s, 3 H), 1.76 (s, 6H), 1.85 (m, 1H) (H$_{6a}$), 1.93 (s, 3H), 2.04 (q, J=6.4 Hz, 4H), 2.36 (s, 3H) (OAc), 2.45 (m, 8H), 2.53 (m, 3H) (H$_{6b}$), 2.77 (t, J=6.4 Hz, 2H), 3.82 (m, 3H), 4.17 (d, J=8.4 Hz, 1H) (H$_{20a}$), 4.31 (d, J=8.4 Hz, 1H) (H$_{20b}$), 4.46 (dd, J=10.6, 6.6 Hz, 1H), 4.77 (d, J=8.8 Hz 1H), 4.98 (m, 3H), (H$_5$), 5.18 (d, J=8.0 Hz, 1H), 5.36 (m, 6H), 5.68 (d, J=6.8 Hz, 1H) (H$_2$), 6.19 (t, J=8.5 Hz, 1H), 6.31 (s, 1H) (H$_{10}$), 7.48 (t, J=7.6 Hz, 2H), 7.60 (t, J=7.6 Hz, 1H), 8.12 (d, J=7.6 Hz, 2 H).

EXAMPLE 11

2'-Linolenoyl-3'-dephenyl-3'-(2-methyl-2-propenyl)-2-debenzoyl-2-(3-methoxybenzoyl)-10-propanoyl-docetaxel (LNA-SB-T-121303)

67% yield; white solid; $^1$H NMR (400 MHz, CDCl$_3$) δ 0.99 (t, J=7.65 Hz, 3H), 1.13 (s, 3H), 1.16 (s, 3H), 1.25 (s, 3H), 1.25-1.35 (m, 8H), 1.33 (s, 9H), 1.66 (m, 3 H), 1.73 (s, 3H), 1.75 (s, 3H), 1.89 (m, 5H), 2.10 (m, 4H), 2.37 (m, 6H), 2.52 (m, 4H), 2.81 (m, 4 H), 3.80 (m, 3H), 3.86 (s, 3H), 4.19 (d, J=8.8 Hz, 1H), 4.35 (d, J=8.8 Hz, 1H), 4.40 (dd, J=10.6, 6.8 Hz, 1 H), 4.75 (d, J=8.8 Hz, 1H), 4.96 (d, J=8.3 Hz, 3H), 5.19 (d, J=8.4 Hz, 1H), 5.36 (m, 6H), 5.67 (d, J=6.8 Hz, 1H), 6.19 (t, J=8.8 Hz, 1H), 6.31 (s, 1H), 7.14 (d, J=6.0 Hz, 1H), 7.38 (t, J=7.6 Hz, 1H), 7.67 (s, 1H), 7.71 (d, J=7.6 Hz, 1H).

EXAMPLE 12

2'-Linolenoyl-3'-dephenyl-3'-(2-methyl-1-propyl)-10-propanoyldocetaxel (LNA-SB-T-1103)

70% yield; m.p. 67-70° C.; $^1$H NMR, (CDCl$_3$) δ 1.00 (m, 9H), 1.20-1.40 (m, 24H), 1.74 (m, 9H), 1.99 (s, 4H), 2.15 (m, 4H), 2.40-2.70 (m, 11H), 2.91 (m, 4H) 3.89 (d, J=7 Hz, 1H), 4.24 (d, J=8.0 Hz, 1H), 4.40 (m, 2H), 4.52 (m, 1H), 4.67 (d, 1H, J=10, Hz), 4.97 (bd, J=1.8 Hz, 1H), 5.00 (bd, J=8 Hz, 1H), 5.45 (m, 6H), 5.73 (d, J=7.0 Hz, 1H), 6.28 (m, 1H), 6.37 (s, 1H), 7.54 (m, 2H), 7.66 (m, 1H), 8.19 (d, J=7.0 Hz, 2H); $^{13}$C NMR (CDCl$_3$) δ 9.3, 9.9, 14.6, 15.0, 20.8, 22.0, 22.5, 22.8, 23.5, 24.9, 25.0, 25.8, 25.9, 26.9, 27.4, 27.8, 28.4, 29.3, 29.4, 29.5, 29.9, 33.9, 35.7, 41.6, 43.4, 45.8, 49.1, 58.7, 71.8, 72.5, 74.6, 75.5, 75.7, 76.7, 79.5, 80.1, 81.2, 84.7, 127.3, 128.1, 128.5, 128.6, 128.9, 129.5, 130.5, 132.3, 132.6, 133.8, 143.7, 155.6, 167.3, 168.8, 169.9, 173.2, 174.9, 204.3.

EXAMPLE 13

In Vivo Evaluation of the Efficacy of the Second-generation Taxoid-Omega-3 Fatty Acid Conjugates Synthesis of Conjugates The second generation taxoids bearing different C-2, C-10, C-3' moieties were synthesized in good to excellent yields starting from 10-deacetylbaccatin III. Coupling of taxoids with DHA was carried out under standard conditions (DIC, DMAP) to give the corresponding conjugates in good yields. The reaction (see reaction A and Table A) takes place at the C-2' OH group.

TABLE A

Reaction A

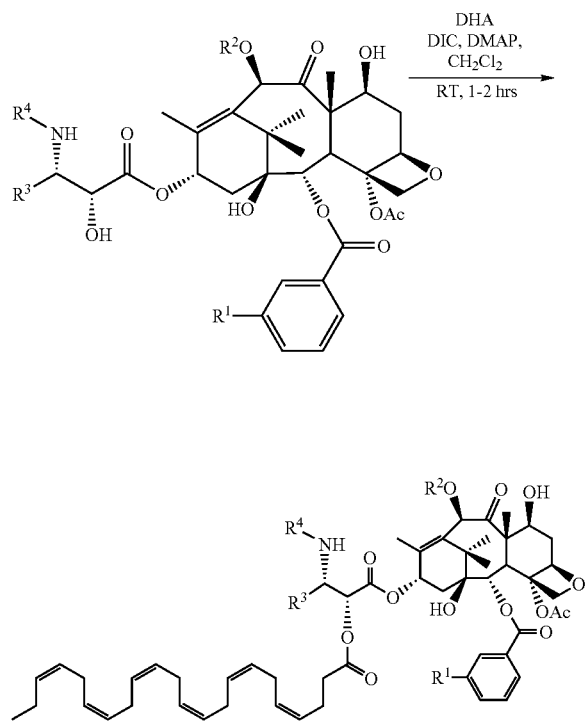

| Taxoid | R[1] | R[2] | R[3] | R[4] | Yield (%) |
|---|---|---|---|---|---|
| DHA-Taxol | H | Ac | $C_6H_6$ | $C_6H_6$ | 98 |
| DHA-Docetaxel | H | OH | $C_6H_6$ | t-Boc | 60 |
| DHA-SB-T-1213 | H | EtCO | Isobutenyl | t-Boc | 76 |
| DHA-SB-T-1103 | H | EtCO | isobutenyl | t-Boc | 56 |
| DHA-SB-T-1214 | H | c-PrCO | isobutenyl | t-Boc | 69 |
| DHA-SB-T-1104 | H | c-PrCO | isobutyl | t-Boc | 73 |
| DHA-SB-T-1216 | H | $Me_2NCO$ | isobutenyl | t-Boc | 87 |
| DHA-SB-T-1217 | H | MeOCO | isobutenyl | t-Boc | 58 |
| DHA-SB-T-121703 | OMe | MeOCO | isobutenyl | t-Boc | 72 |
| DHA-SB-T-121303 | OMe | EtCO | isobutenyl | t-Boc | 76 |
| DHA-SB-T-11033 | OMe | Ac | isobutenyl | t-Boc | 72 |

Animals and Tumor Xenografts:

Female severe combined immune deficient, (SCID) mice aged six to eight weeks were obtained from either the in-house breeding facility at Roswell Park Cancer Institute or Taconic (Germantown, N.Y.). All aspects of animal care complied with the Institutional Animal Care and Use Committee guidelines. Either the human ovarian tumor A121, which does not express the MDR protein pgp, or the human colon tumor DLD-1 which does express pgp, were used. Tumors were initiated by implantation of approximately 50 mg of non-necrotic tumor fragments on the right flank using a 12-guage trocar needle. Chemotherapy was started when the tumor was established as a palpable mass, (approximately 50-100 mm³ size). Therapy consisted of i.v. injections through the tail vein, given four times, three days apart. Each drug treatment group or drug free vehicle consisted of 4-5 mice per group, untreated controls contained 10 mice per group.

Drug Preparation for In Vivo Experiments

Paclitaxel and DHA-Paclitaxel was prepared as a 7.5 mg/mL stock solution in equal parts of Cremophor ELP (BASF, Ludwigshafen, Germany) and absolute ethanol. These were used for comparison purposes. DHA-taxoids and other omega-3 fatty acid-taxoids were prepared as a 30 mg/mL stock solution in equal parts of Tween 80 (polyoxyethylene-sorbitan monooleate; purchased from Sigma Chemical Company) and absolute ethanol. To stablize the formulation of the DHA-taxoids and other omega-3 fatty acid-taxoids, antioxidants, L-ascorbic acid (3.9 mM) and α-tocopherol (2.0 mM), were added. Each stock solution was further diluted before use in 0.9% NaCl (saline) so that the appropriate concentration of each drug could be injected i.v. via the tail vein, in a volume of approximately 0.4 mL for a 20 g mouse. Each drug was administered once a day on day 5, 8, and 11.

In Vivo Tumor Growth Assay

For each animal, the tumor length (l) and width (w), each in mm, were measured using electronic calipers and recorded every 3-4 days. Tumor volume (v), in mm³, was calculated using the formula: $v=0.4(l \times w^2)$. The time in days to the pre-determined target tumor volume of 600 mm³ was linearly interpolated from a plot of log(volume) versus time. Statistically significant differences in tumor volumes between control and drug-treated mice were determined by the Cox-Mantel test. For the Cox-Mantel test, the time-to-event data for animals that did not reach the target tumor volume, either because of long-term cure (defined as those animals that were still alive at the conclusion of the experiment whose tumors either completely regressed or did not reach the pre-set target volume) or early death due to drug toxicity, were treated as censored data. All statistical tests were two-sided.

Results

Second-generation taxoid-fatty acids conjugates were evaluated for their antitumor activity against the drug-resistant human colon tumor xenografts (pgp+) DLD-1 and the drug sensitive human ovarian tumor xenograft (pgp−) A121 in SCID mice (Table 1). Median tumor size is shown in FIG. 1.

TABLE 1

Antitumor effect of DHA-Taxoid conjugates delivered i.v. to SCID mice bearing a pgp+ human colon tumor xenograft, DLD-1

| Treatment[1] i.v. | Total Dose (mg/kg) | Dose/inj (mg/kg) | Days to 600 mm³ Median (range) | PValue[2] (Control) | Growth Delay (days) | Toxicity[3] | Tumor[4] free mice/ Group |
|---|---|---|---|---|---|---|---|
| Control | 0 | 0 | 14 (14-22) | — | — | 0 | 0/7 |
| Vehicle-Crem | 0 | 0 | 14 (11-18) | .556 | — | 0 | 0/3 |
| Vehicle-Tween | 0 | 0 | 18 (14-18) | .896 | — | 0 | 0/3 |
| Paclitaxel | 60 | 20 | 22 (18-24) | .069 | 8 | 0 | 0/3 |
| IDN-5109 | 150 | 50 | 46 (39-108) | .005 | 32 | 0 | 0/3 |
| DHA-Paclitaxel | 240 | 80 | 18 (14-22) | .355 | 4 | 0 | 0/5 |
| DHA-SB-T-1213 | 75 | 25 | 68 (47-112) | <.001 | 54 | 0 | 0/5 |
| DHA-SB-T-1103 | 75 | 25 | 18 (14-21) | .870 | 4 | 0 | 0/5 |
| DHA-SB-T-1214 | 240 | 80 | >201 | <.001 | >187 | 0 | 5/5 |
| DHA-SB-T-1104 | 240 | 80 | 18 (14-19) | .437 | 4 | 0 | 0/5 |
| DHA-IDN-5109 | 150 | 50 | 14 (14-18) | .759 | 0 | 0 | 0/5 |
| DHA-Docetaxel | 75 | 25 | 31 (25-37) | .002 | 17 | 0 | 0/4 |
| DHA-Docetaxel | 150 | 50 | 48 (46-48) | .002 | 34 | 0 | 0/4 |

[1]Treatment given i.v. to SCID mice on day 5, 8 and 11 after DLD-1 human colon tumor implant. Paclitaxel and DHA-paclitaxel formulated in Cremophor:EtOH; IND5109 and DHA-taxoid conjugates formulated in Tween:EtOH.
[2]Based on comparison of each group vs. control using the Cox-Mantle Test.
[3]Number of animals who either died or lost greater than 20% body weight.
[4]SCID mice with tumors less than 600 mm³ on day 201.

As Table 1 clearly indicates, the second-generation taxoid-DHA conjugate, DHA-SB-T-1214 exhibits a remarkable antitumor effect on drug-resistant human colon tumor xenografts in SCID mice. For DHA-SB-T-1214, all mice were alive on day 201 and no trace of tumor was detected in DHA-SB-T-1214 treated mice. DHA-SB-T-1213 caused a 54-day delay in tumor growth. These results clearly demonstrate the exceptional efficacy of DHA-second-generation taxoids.

Figure 2:
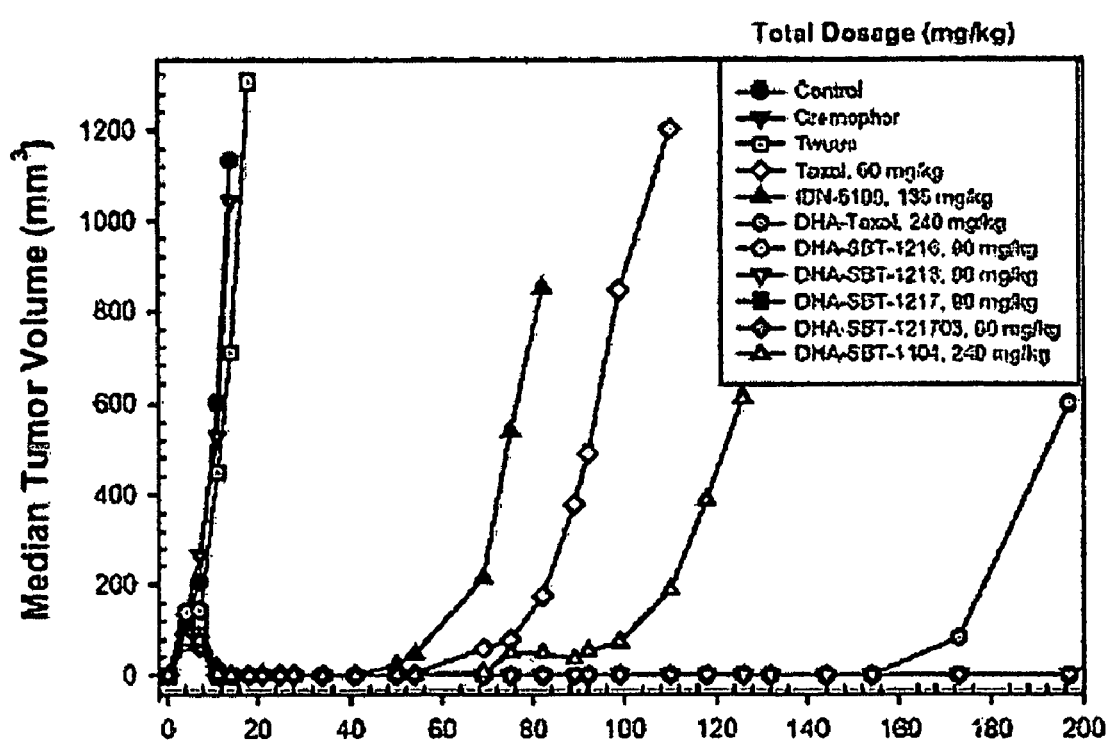
FIG. 2. Effect of DHA-Taxoid Conjugated on Human Ovarian Tumor Exograft (pgp−) A121.

DHA-SB-T-1213 also showed excellent results against human ovarian tumor xenograft (pgp−) A121 (see FIG. 2 and Table 2). When a total dose of 90 mg/kg was applied, the conjugate showed >186-day delay in tumor growth in 4 surviving mice (4 of 5). In addition, DHA-SB-T-1216 and DHA-SB-T-1104 also demonstrated effective tumor growth delay.

TABLE 2

Antitumor effect of DHA-Taxoid conjugates delivered i.v. to scid mice bearing a human ovarian tumor xenograft, A121

| Treatment[1] i.v. | Total Dose (mg/kg) | Dose/inj (mg/kg) | Days to 600 mm³ Median (range) | PValue[2] (Control) | Growth Delay (days) | Toxicity[3] | Tumor[4] free mice/ Group |
|---|---|---|---|---|---|---|---|
| Control | 0 | 0 | 11 (11-14) | — | — | 0 | 0/10 |
| Vehicle-Crem | 0 | 0 | 14 (11-14) | .679 | 3 | 0 | 0/5 |
| Vehicle-Tween | 0 | 0 | 14 (14-18) | .075 | 3 | 0 | 0/5 |
| Paclitaxel | 60 | 20 | 94 (82-140) | <.001 | 83 | 0 | 0/5 |
| DHA-Paclitaxel | 240 | 80 | 197 (183->197) | <.001 | 186 | 0 | 2/5 |
| DHA-SB-T-1216 | 90 | 30 | >197 | .002 | >186 | 4 | 1/5 |
| DHA-SB-T-1213 | 90 | 30 | >197 | <.001 | >186 | 1 | 4/5 |
| DHA-SB-T-1104 | 240 | 80 | 126 (78-195) | <.001 | 115 | 0 | 0/5 |

[1]Treatment given i.v. to SCID mice on day 5 after A121 human ovarian tumor implant. Paclitaxel and DHA-paclitaxel formulated in Cremophor: EtOH; DHA-taxoid conjugates formulated in Tween: EtOH
[2]Based on comparison of each group vs. control using the Cox-Mantle Test
[3]Number of animals who either died or lost greater than 20% body weight
[4]SCID mice with no palpable tumor on day 197.

What is claimed is:

1. In a conjugate comprising a taxoid and an omega-3 fatty acid, the improvement wherein the taxoid is a second-generation taxoid having the following structure:

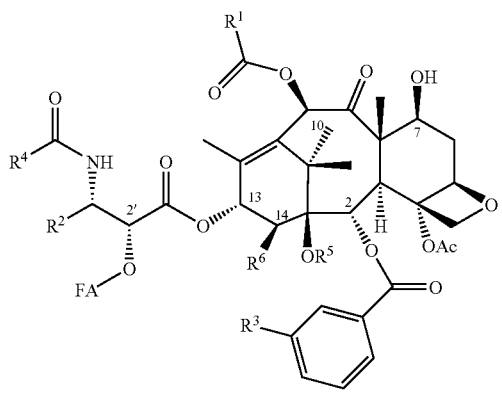

wherein $R^1$ represents C1-C6 alkyl or alkenyl, dialklylamino or alkylamino, or alkoxy;

$R^2$ represents $C_3$-$C_5$ alkyl or alkenyl or trifluoromethyl;

$R^3$ represents H, methyl, methoxy, chloro, fluoro or azido;

$R^4$ represents C3-C6 cycloalkyl or cycloakenyl or an alkoxy;

$R^5$ and $R^6$ are both hydrogens or $R^5$ and $R^6$ together represent oxycarbonyl, forming thereby a cyclic carbonate FA represents an omega-3 fatty acid.

2. A conjugate according to claim 1, wherein the second-generation taxoid is SB-T-1214 having the following structure:

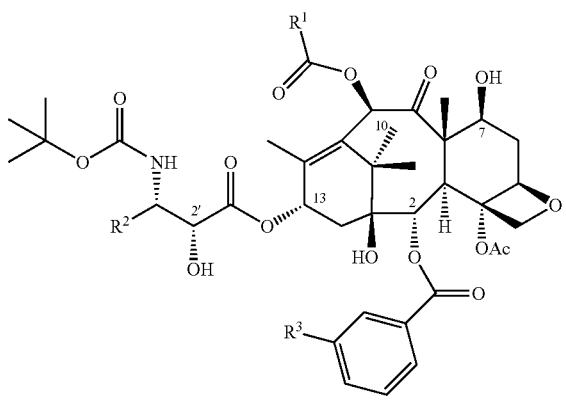

wherein $R^1$ is cyclopropyl, $R^2$ is 2-methyl-1-propenyl, and $R^3$ is H.

3. A conjugate according to claim 1, wherein the second-generation taxoid is SB-T-1213 having the following structure:

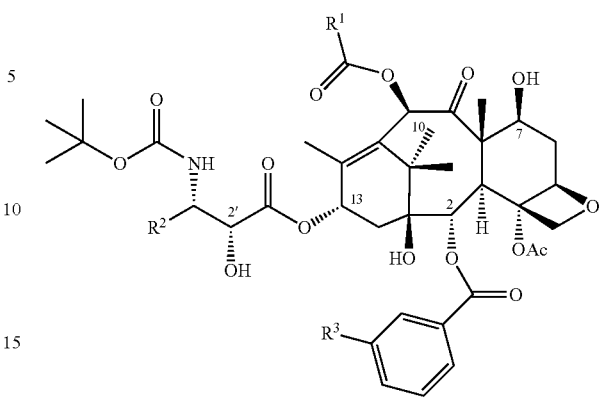

wherein: $R^1$ is $C_2H_5$, $R^2$ is 2-methyl-1-propenyl, and $R^3$ is H.

4. A conjugate according to claim 1, wherein the second-generation taxoid is SB-T-1216 having the following structure:

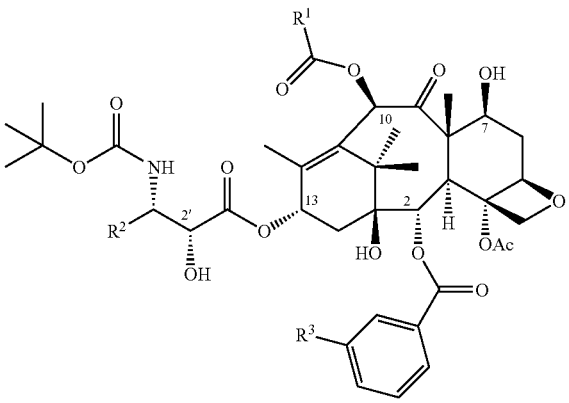

wherein: $R^1$ is $(CH_3)_2N$, $R^2$ is 2-methyl-1-propenyl, and $R^3$ is H.

5. A conjugate according to claim 1, wherein the second-generation taxoid is SB-T-1103 having the following structure:

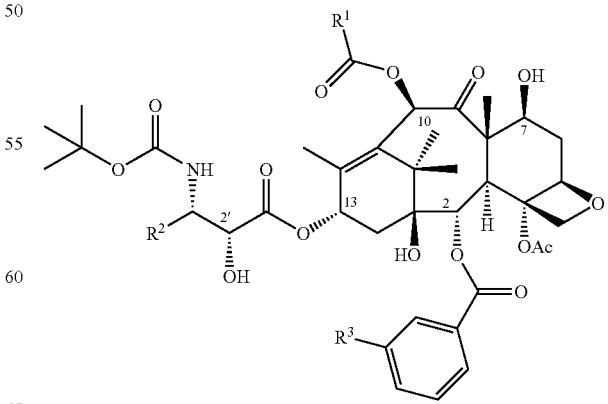

wherein: $R^1$ is $C_2H_5$, $R^2$ is 2-methylpropyl, and $R^3$ is H.

6. A conjugate according to claim 1, wherein the second-generation taxoid is ortataxel.

7. A conjugate according to claim 1, wherein the second-generation taxoid is SB-T-11033 having the following structure:

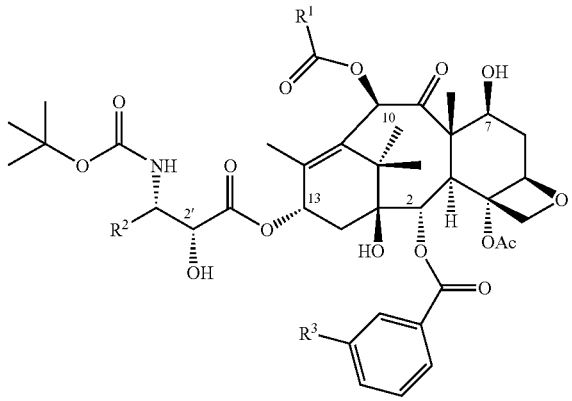

wherein: $R^1$ is $C_2H_5$, $R^2$ is 2-methylpropyl, and $R^3$ is $CH_3O$.

8. A conjugate according to claim 1, wherein the second-generation taxoid is SB-T-1104 having the following structure:

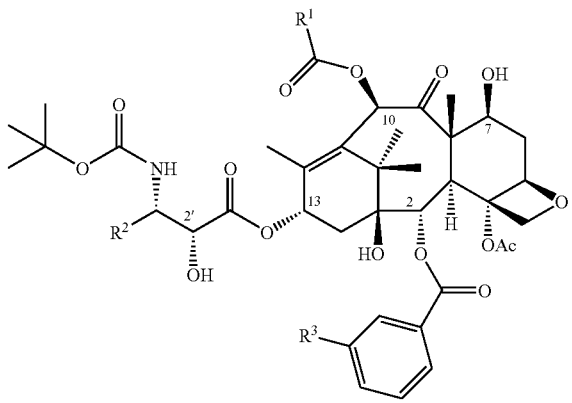

wherein: $R^1$ is cyclopropyl, $R^2$ is 2-methylpropyl, and $R^3$ is H.

9. A conjugate according to claim 1, wherein the second-generation taxoid is SB-T-11043 having the following structure:

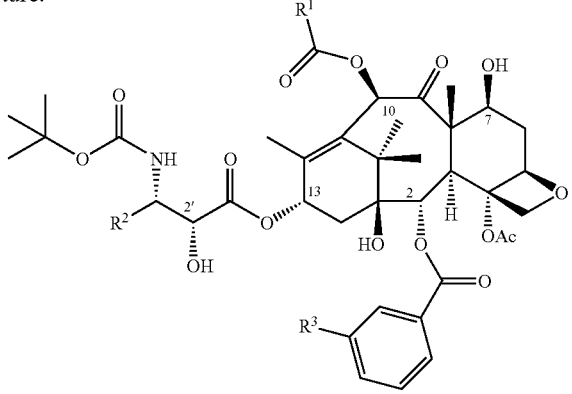

wherein: $R^1$ is cyclopropyl, $R^2$ is 2-methylpropyl, and $R^3$ is $CH_3O$.

10. A conjugate according to claim 1, wherein the second-generation taxoid is SB-T-1107 having the following structure:

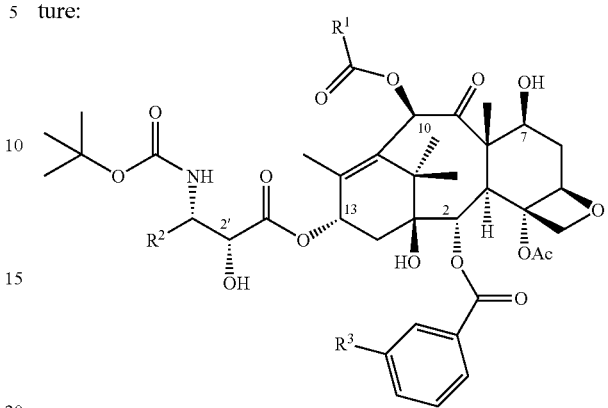

wherein: $R^1$ is $CH_3O$, $R^2$ is 2-methylpropyl, and $R^3$ is H.

11. A conjugate according to claim 1, wherein the second-generation taxoid is SB-T-11073 having the following structure:

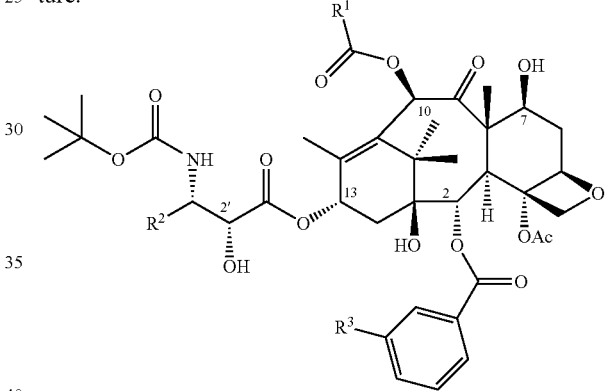

wherein: $R^1$ is $CH_3O$, $R^2$ is 2-methylpropyl, and $R^3$ is $CH_3O$.

12. A conjugate according to claim 1, wherein the second-generation taxoid is SB-T-121303 having the following structure:

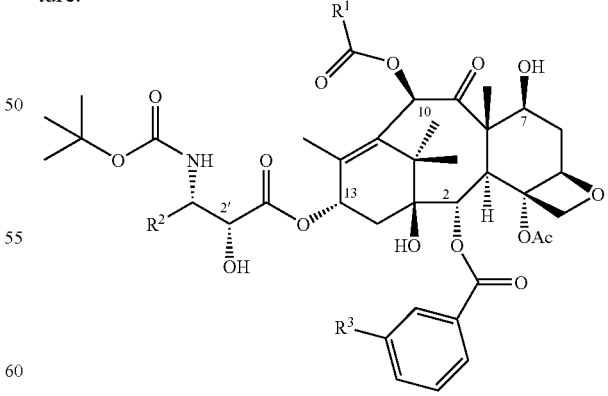

wherein: $R^1$ is $C_2H_5$, $R^2$ is 2-methyl-1-propenyl, and $R^3$ is $CH_3O$.

13. A conjugate according to claim 1, wherein the second-generation taxoid is SB-T-121403 having the following structure:

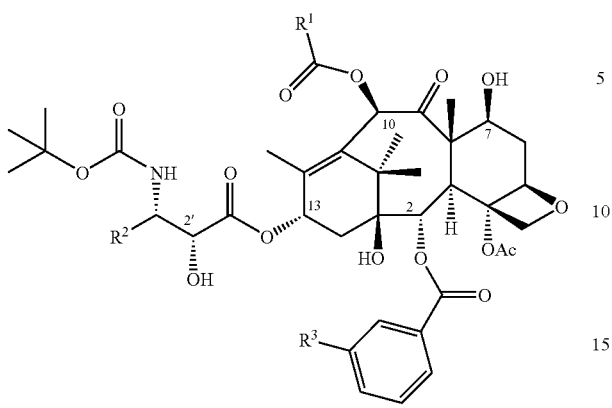

wherein: R¹ is cyclopropyl, R² is 2-methyl-1-propenyl, and R³ is CH₃O.

14. A conjugate according to claim 1, wherein the second-generation taxoid is SB-T-121603 having the following structure:

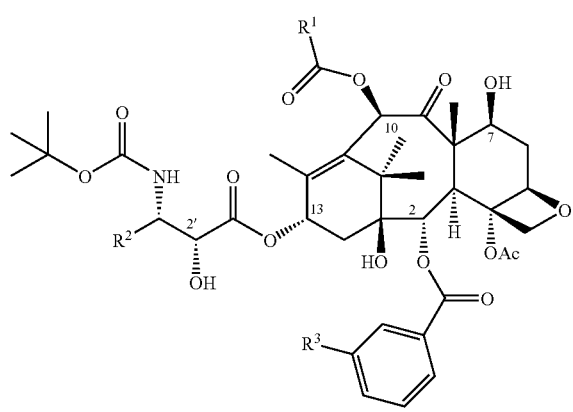

wherein: R¹ is (CH₃)₂N, R² is 2-methyl-1-propenyl, and R³ is CH₃O.

15. A conjugate according to claim 1, wherein the second-generation taxoid is SB-T-121703 having the following structure:

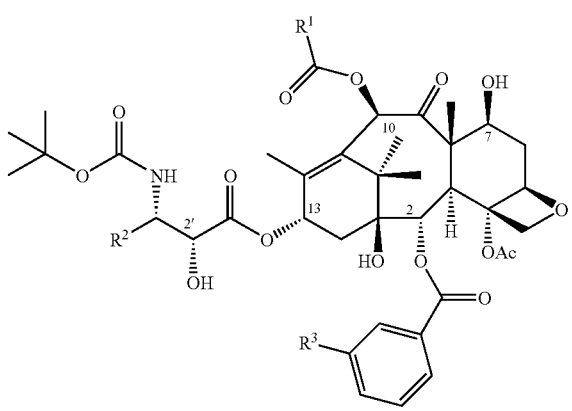

wherein: R¹ is CH₃O, R² is 2-methyl-1-propenyl, and R³ is CH₃O.

16. A conjugate according to claim 1, wherein the second-generation taxoid is SB-T-12821 having the following structure:

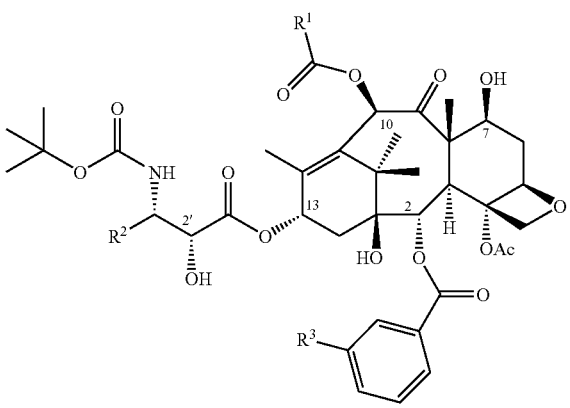

wherein: R¹ is (CH₃)₂N, R² is trifluoromethyl, and R³ is H.

17. A conjugate according to claim 1, wherein the second-generation taxoid is SB-T-128221-3 having the following structure:

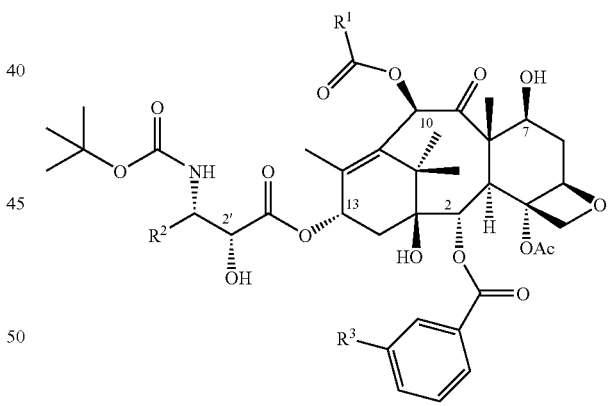

wherein: R¹ is C₂H₅, R² is trifluoromethyl, and R³ is CH₃O.

18. A conjugate according to claim 1, wherein the omega-3 fatty acid is docosahexanoic acid.

19. A conjugate according to claim 1, wherein the omega-3 fatty acid is eicosapentaenoic acid.

20. A conjugate according to claim 1, wherein the omega-3 fatty acid is α-linolenic acid.

21. In a pharmaceutical composition comprising a conjugate comprising a taxoid and an omega 3-fatty acid, the improvement wherein the taxoid is a second-generation taxoid having the following structure:

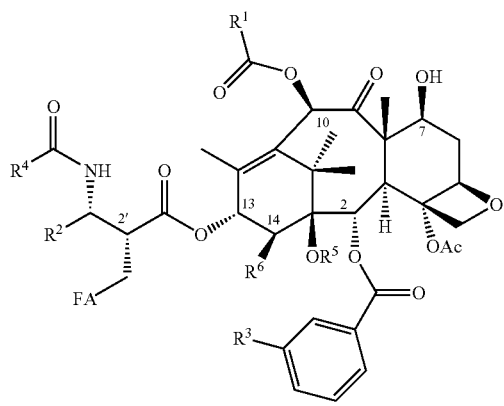

wherein R¹ represents C1-C6 alkyl or alkenyl, dialkly-lamino or alkylamino, or alkoxy;

R² represents $C_3$-$C_5$ alkyl or alkenyl or trifluoromethyl;

R³ represents H, methyl, methoxy, chloro, fluoro or azido;

R⁴ represents C3-C6 cycloalkyl or cycloakenyl or an alkoxy;

R⁵ and R⁶ are both hydrogens or R⁵ and R⁶ together represent oxycarbonyl, forming thereby a cyclic carbonate FA represents an omega-3 fatty acid.

22. A pharmaceutical composition according to claim 21, wherein the second-generation taxoid is ortataxel.

23. A pharmaceutical composition according to claim 21, wherein the second-generation taxoid is SB-T-121303 having the following structure:

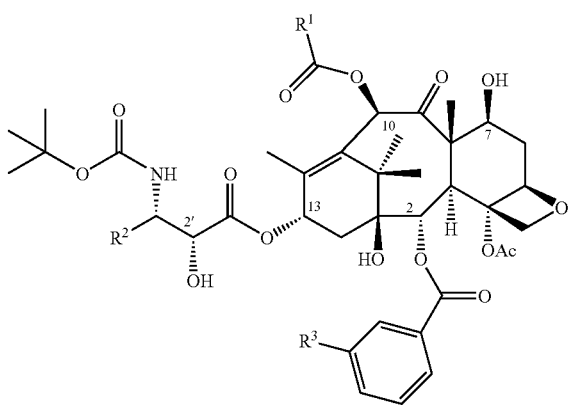

wherein: R¹ is $C_2H_5$, R² is 2-methyl-1-propenyl, and R³ is $CH_3O$.

24. A pharmaceutical composition according to claim 21, wherein the second-generation taxoid is SB-T-1103 having the following structure:

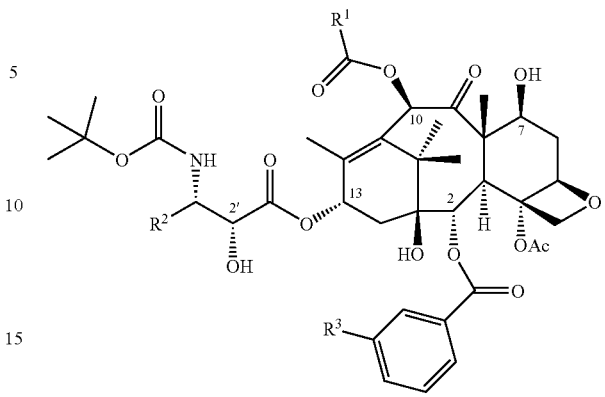

wherein: R¹ is $C_2H_5$, R² is 2-methylpropyl, and R³ is H.

25. A pharmaceutical composition according to claim 21, wherein the second-generation taxoid is SB-T-1214 having the following structure:

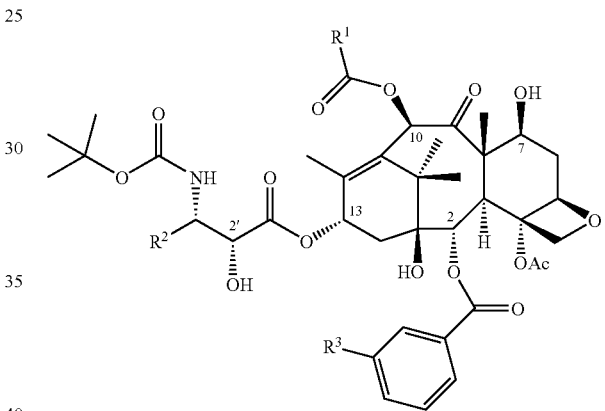

wherein R¹ is cyclopropyl, R² is 2-methyl-1-propenyl, and R³ is H.

26. A pharmaceutical composition according to claim 21, wherein the second-generation taxoid is SB-T-1216 having the following structure:

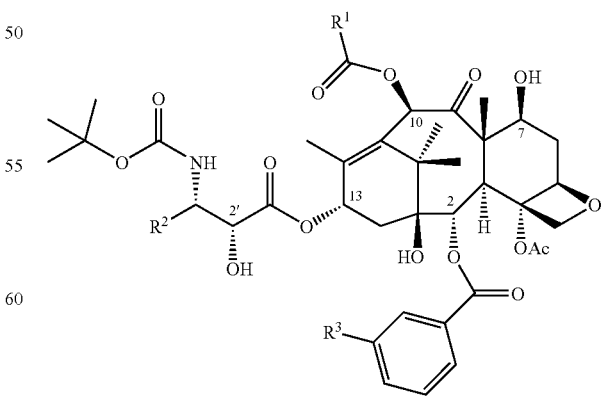

wherein: R¹ is $(CH_3)_2N$, R² is 2-methyl-1-propenyl, and R³ is H.

27. A pharmaceutical composition according to claim 21, wherein the second-generation taxoid is SB-T-11033 having the following structure:

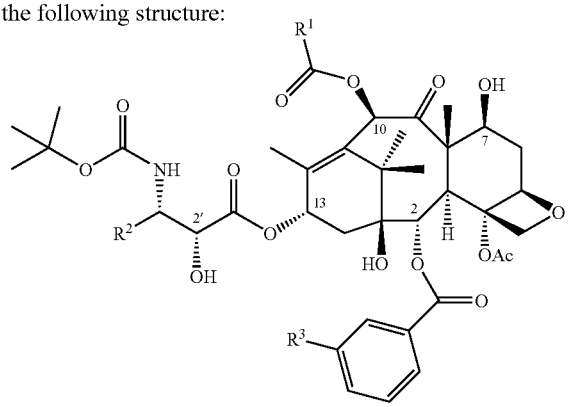

wherein: R$^1$ is C$_2$H$_5$, R$^2$ is 2-methylpropyl, and R$^3$ is CH$_3$O.

28. A pharmaceutical composition according to claim 21, wherein the second-generation taxoid is SB-T-1104 having the following structure:

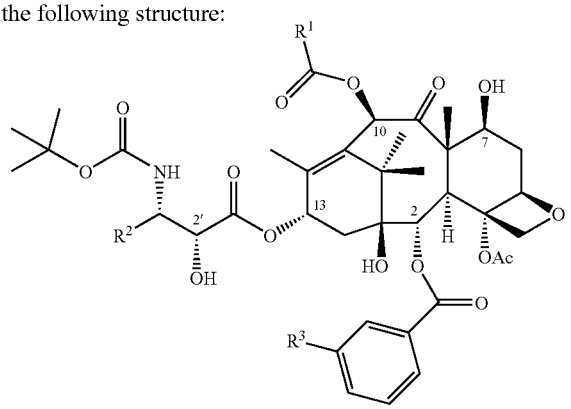

wherein: R$^1$ is cyclopropyl, R$^2$ is 2-methylpropyl, and R$^3$ is H.

29. A pharmaceutical composition according to claim 21, wherein the second-generation taxoid is SB-T-11043 having the following structure:

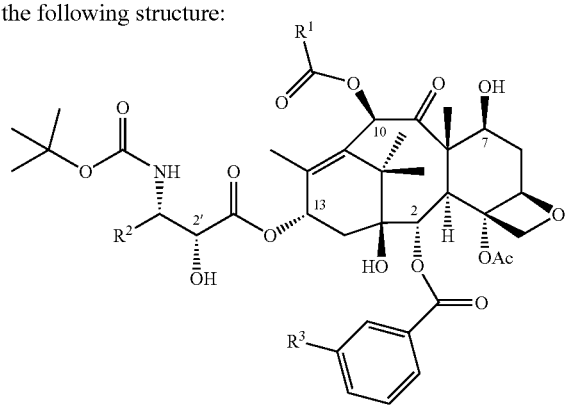

wherein: R$^1$ is cyclopropyl, R$^2$ is 2-methylpropyl, and R$^3$ is CH$_3$O.

30. A pharmaceutical composition according to claim 21, wherein the second-generation taxoid is SB-T-1107 having the following structure:

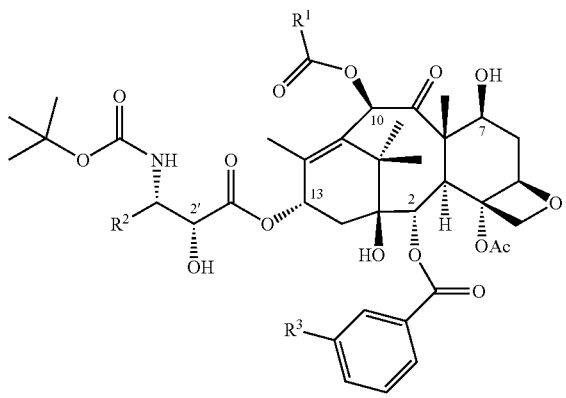

wherein: R$^1$ is CH$_3$O, R$^2$ is 2-methylpropyl, and R$^3$ is H.

31. A pharmaceutical composition according to claim 21, wherein the second-generation taxoid is SB-T-11073 having the following structure:

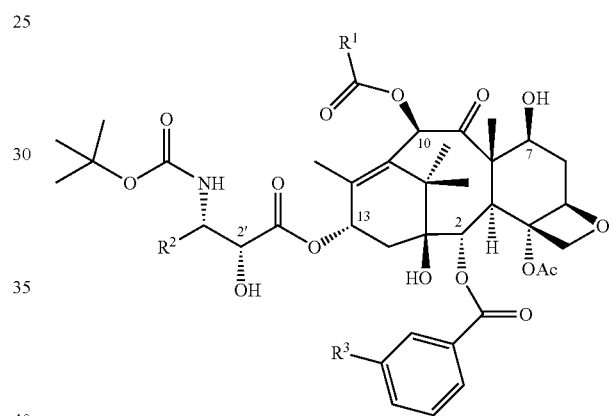

wherein: R$^1$ is CH$_3$O, R$^2$ is 2-methylpropyl, and R$^3$ is CH$_3$O.

32. A pharmaceutical composition according to claim 21, wherein the second-generation taxoid is SB-T-1213 having the following structure:

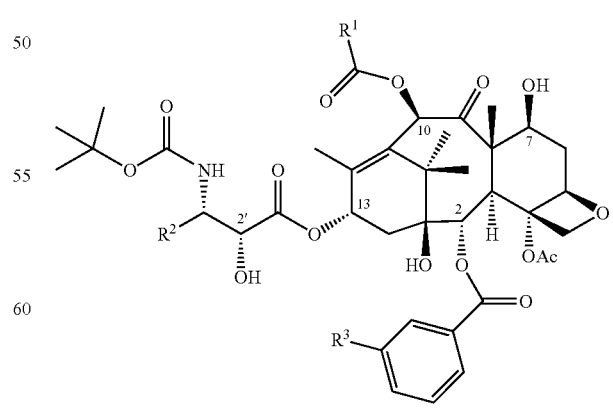

wherein: R$^1$ is C$_2$H$_5$, R$^2$ is 2-methyl-1-propenyl, and R$^3$ is H.

33. A pharmaceutical composition according to claim 21, wherein the second-generation taxoid is SB-T-121403 having the following structure:

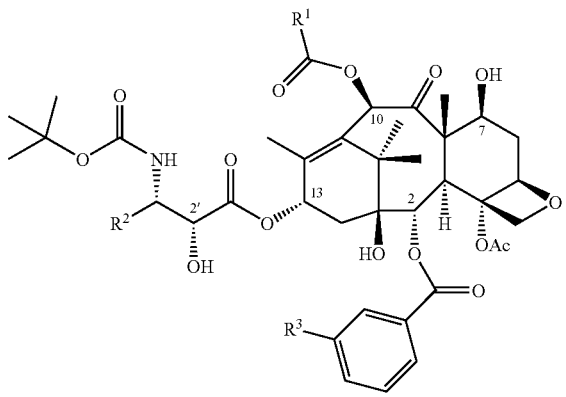

wherein: $R^1$ is cyclopropyl, $R^2$ is 2-methyl-1-propenyl, and $R^3$ is $CH_3O$.

34. A pharmaceutical composition according to claim 21, wherein the second-generation taxoid is SB-T-121603 having the following structure:

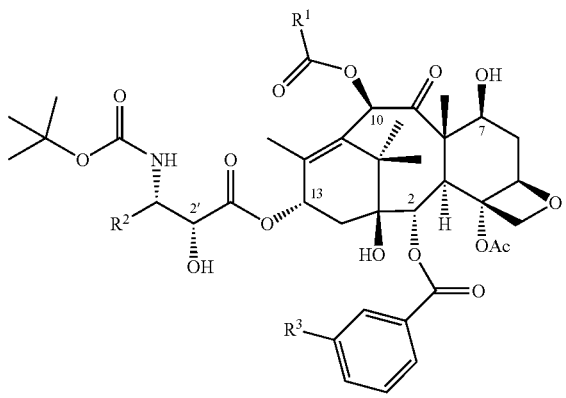

wherein: $R^1$ is $(CH_3)_2N$, $R^2$ is 2-methyl-1-propenyl, and $R^3$ is $CH_3O$.

35. A pharmaceutical composition according to claim 21, wherein the second-generation taxoid is SB-T-121703 having the following structure:

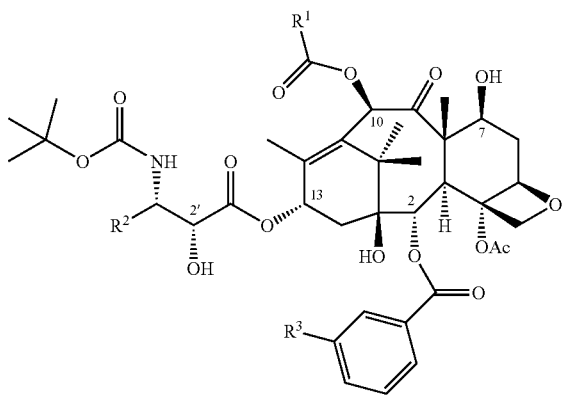

wherein: $R^1$ is $CH_3O$, $R^2$ is 2-methyl-1-propenyl, and $R^3$ is $CH_3O$.

36. A pharmaceutical composition according to claim 21, wherein the second-generation taxoid is SB-T-12821 having the following structure:

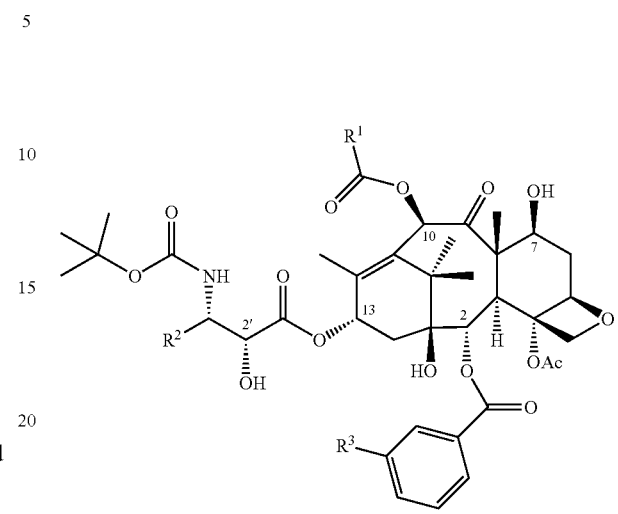

wherein: $R^1$ is $(CH_3)_2N$, $R^2$ is trifluoromethyl, and $R^3$ is H.

37. A pharmaceutical composition according to claim 21, wherein the second-generation taxoid is SB-T-128221-3 having the following structure:

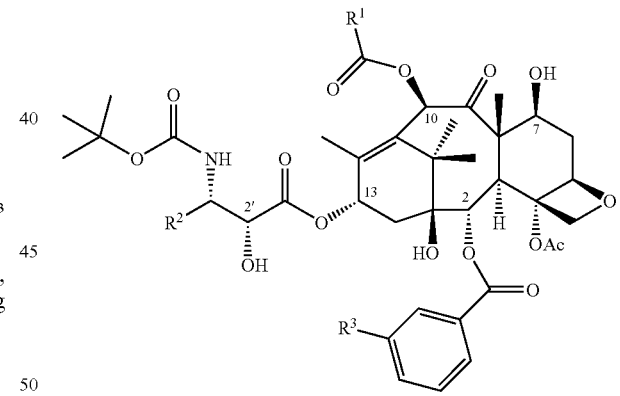

wherein: $R^1$ is $C_2H_5$, $R^2$ is trifluoromethyl, and $R^3$ is $CH_3O$.

38. A pharmaceutical composition according to claim 21, wherein the omega-3 fatty acid is docosahexanoic acid.

39. A pharmaceutical composition according to claim 21, wherein the omega-3 fatty acid is eicosapentaenoic acid.

40. A pharmaceutical composition according to claim 21, wherein the omega-3 fatty acid is α-linolenic acid.

41. In a method for treating cancer in a human in need thereof, the method comprising administering an effective amount of a conjugate comprising a taxoid and an omega 3-fatty acid, the improvement wherein the taxoid is a second-generation taxoid having the following structure:

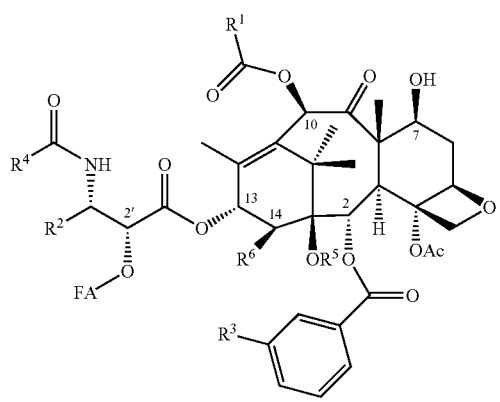

wherein $R^1$ represents C1-C6 alkyl or alkenyl, dialkylamino or alkylamino, or alkoxy;

$R^2$ represents $C_3$-$C_5$ alkyl or alkenyl or trifluoromethyl;

$R^3$ represents H, methyl, methoxy, chloro, fluoro or azido;

$R^4$ represents C3-C6 cycloalkyl or cycloakenyl or an alkoxy;

$R^5$ and $R^6$ are both hydrogens or $R^5$ and $R^6$ together represent oxycarbonyl, forming thereby a cyclic carbonate FA represents an omega-3 fatty acid.

42. A method according to claim 41, wherein the second-generation taxoid is ortataxel.

43. A method according to claim 41, wherein the second-generation taxoid is SB-T-121303 having the following structure:

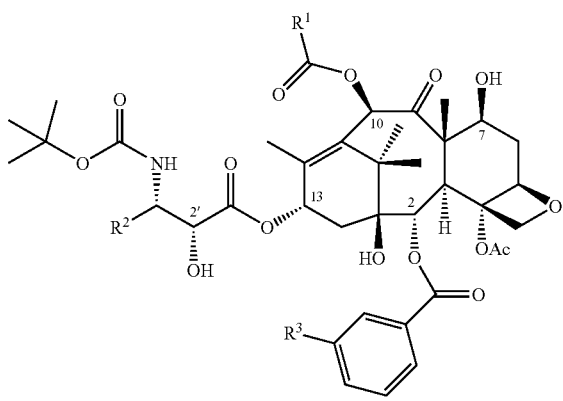

wherein: $R^1$ is $C_2H_5$, $R^2$ is 2-methyl-1-propenyl, and $R^3$ is $CH_3O$.

44. A method according to claim 41, wherein the second-generation taxoid is SB-T-1103 having the following structure:

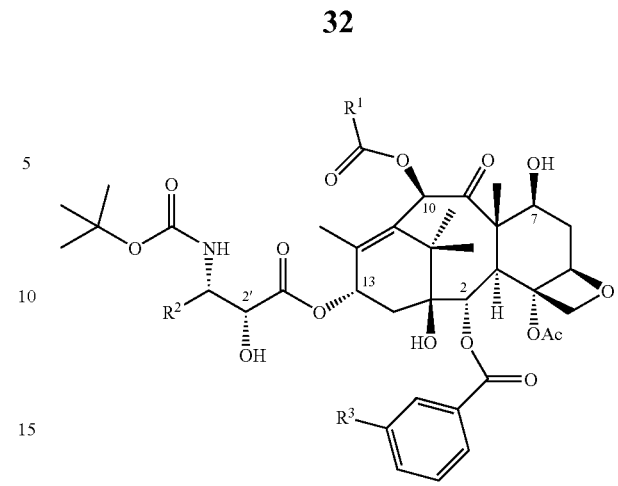

wherein: $R^1$ is $C_2H_5$, $R^2$ is 2-methylpropyl, and $R^3$ is H.

45. A method according to claim 41, wherein the second-generation taxoid is SB-T-1214 having the following structure:

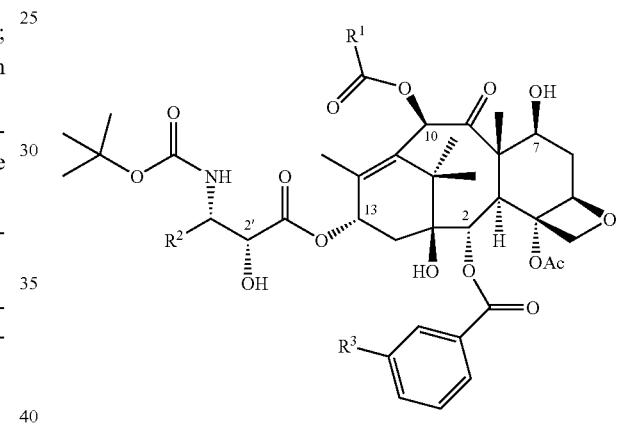

wherein $R^1$ is cyclopropyl, $R^2$ is 2-methyl-1-propenyl, and $R^3$ is H.

46. A method according to claim 41, wherein the second-generation taxoid is SB-T-1216 having the following structure:

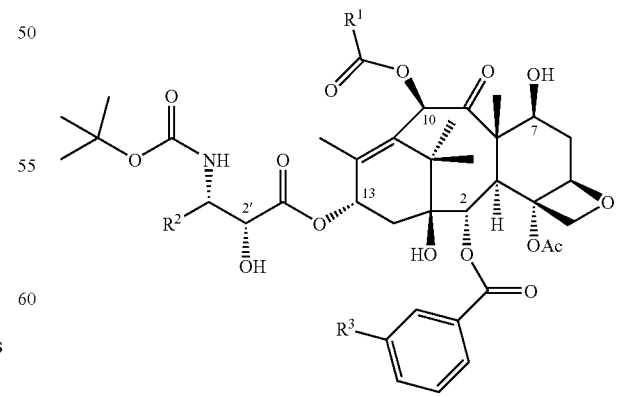

wherein: $R^1$ is $(CH_3)_2N$, $R^2$ is 2-methyl-1-propenyl, and $R^3$ is H.

47. A method according to claim 41, wherein the second-generation taxoid is SB-T-11033 having the following structure:

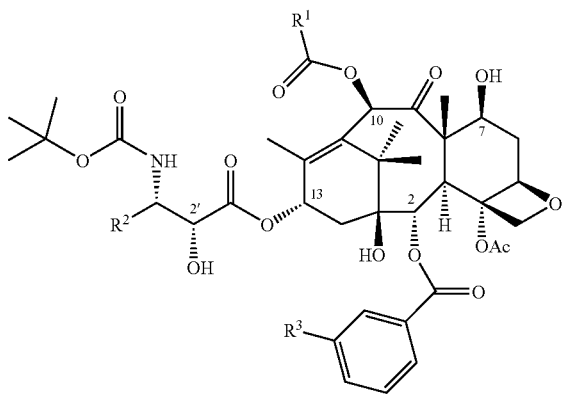

wherein: $R^1$ is $C_2H_5$, $R^2$ is 2-methylpropyl, and $R^3$ is $CH_3O$.

48. A method according to claim 41, wherein the second-generation taxoid is SB-T-1104 having the following structure:

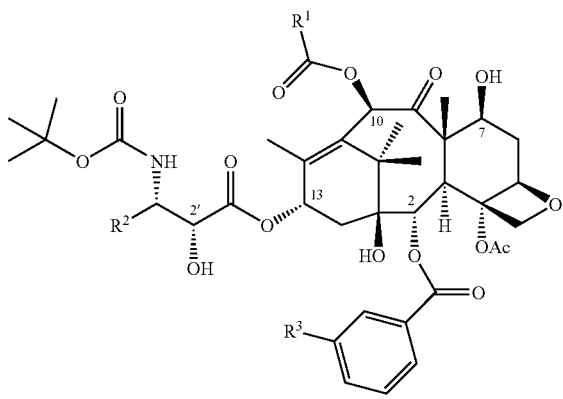

wherein: $R^1$ is cyclopropyl, $R^2$ is 2-methylpropyl, and $R^3$ is H.

49. A method according to claim 41, wherein the second-generation taxoid is SB-T-11043 having the following structure:

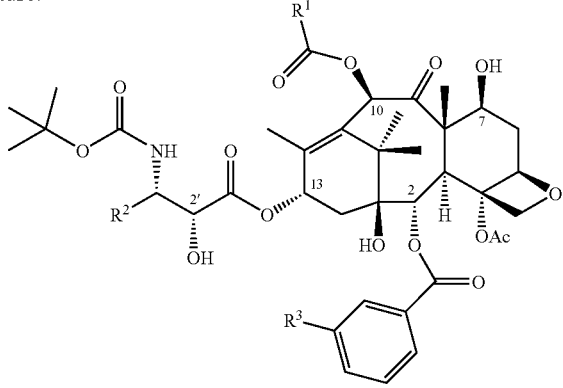

wherein: $R^1$ is cyclopropyl, $R^2$ is 2-methylpropyl, and $R^3$ is $CH_3O$.

50. A method according to claim 41, wherein the second-generation taxoid is SB-T-1107 having the following structure:

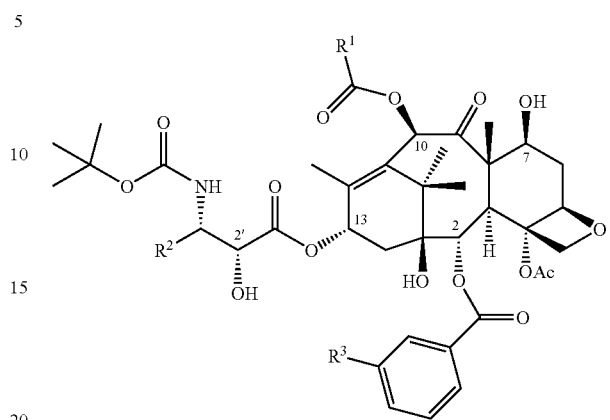

wherein: $R^1$ is $CH_3O$, $R^2$ is 2-methylpropyl, and $R^3$ is H.

51. A method according to claim 41, wherein the second-generation taxoid is SB-T-11073 having the following structure:

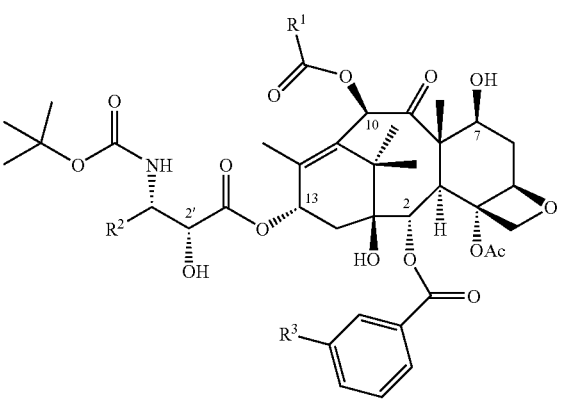

wherein: $R^1$ is $CH_3O$, $R^2$ is 2-methylpropyl, and $R^3$ is $CH_3O$.

52. A method according to claim 41, wherein the second-generation taxoid is SB-T-1213 having the following structure:

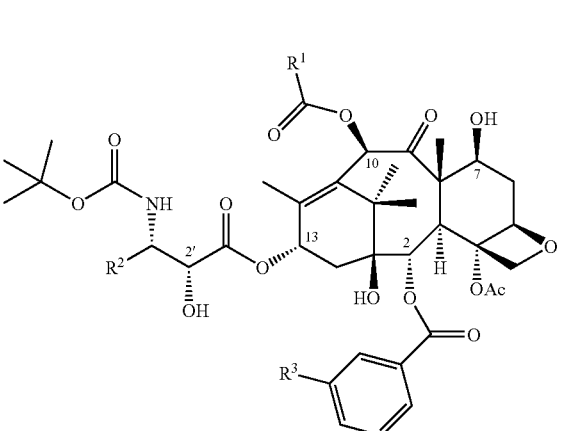

wherein: $R^1$ is $C_2H_5$, $R^2$ is 2-methyl-1-propenyl, and $R^3$ is H.

53. A method according to claim 41, wherein the second-generation taxoid is SB-T-121403 having the following structure:

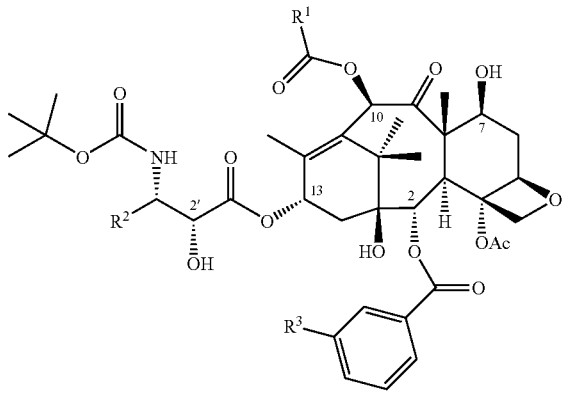

wherein: $R^1$ is cyclopropyl, $R^2$ is 2-methyl-1-propenyl, and $R^3$ is $CH_3O$.

54. A method according to claim 41, wherein the second-generation taxoid is SB-T-121603 having the following structure:

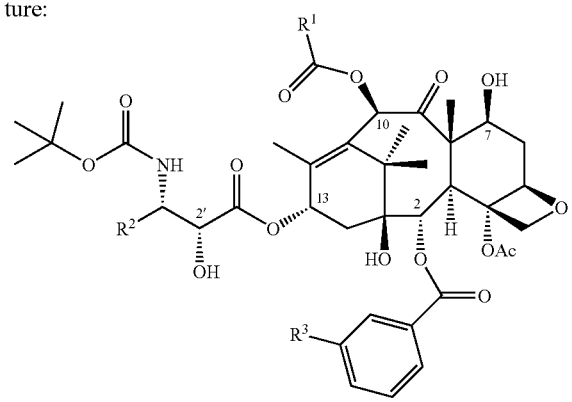

wherein: $R^1$ is $(CH_3)_2N$, $R^2$ is 2-methyl-1-propenyl, and $R^3$ is $CH_3O$.

55. A method according to claim 41, wherein the second-generation taxoid is SB-T-121703 having the following structure:

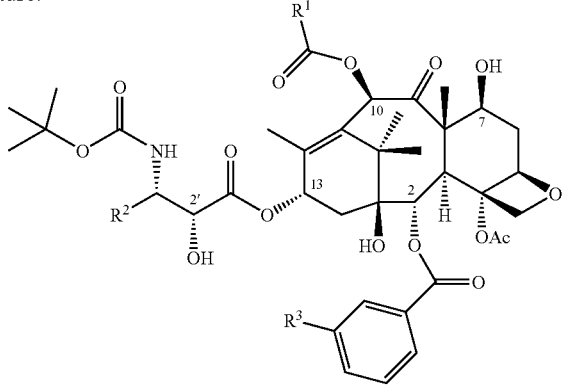

wherein: $R^1$ is $CH_3O$, $R^2$ is 2-methyl-1-propenyl, and $R^3$ is $CH_3O$.

56. A method according to claim 41, wherein the second-generation taxoid is SB-T-12821 having the following structure:

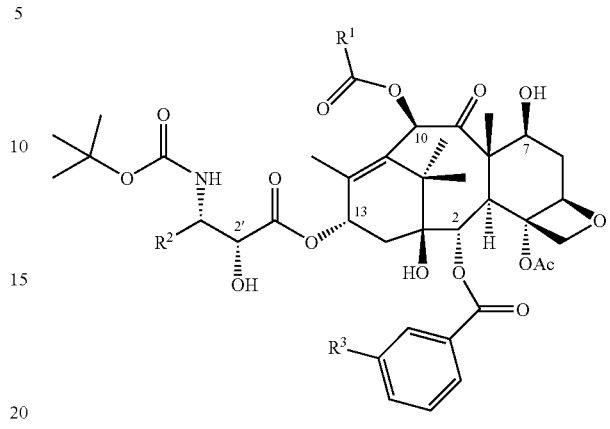

wherein: $R^1$ is $(CH_3)_2N$, $R^2$ is trifluoromethyl, and $R^3$ is H.

57. A method according to claim 41, wherein the second-generation taxoid is SB-T-128221-3 having the following structure:

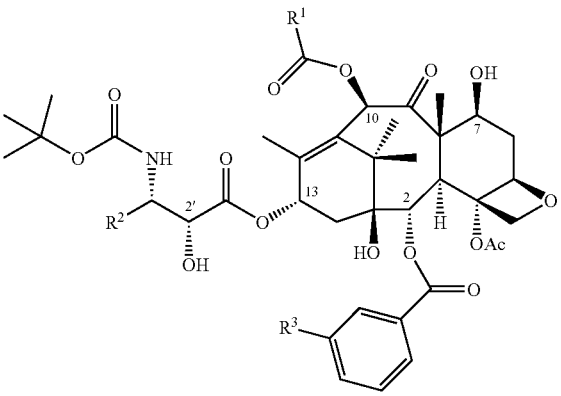

wherein: $R^1$ is $C_2H_5$, $R^2$ is trifluoromethyl, and $R^3$ is $CH_3O$.

58. A method according to claim 41, wherein the omega-3 fatty acid is docosahexanoic acid.

59. A method according to claim 41, wherein the omega-3 fatty acid is eicosapentaenoic acid.

60. A method according to claim 41, wherein the omega-3 fatty acid is α-linolenic acid.

61. A method according to claim 41, wherein the cancer is breast cancer.

62. A method according to claim 41, wherein the cancer is ovarian cancer.

63. A method according to claim 41, wherein the cancer is lung cancer.

64. A method according to claim 41, wherein the cancer is head cancer.

65. A method according to claim 41, wherein the cancer is neck cancer.

66. A method according to claim 41, wherein the cancer is colon cancer.

67. A method according to claim 41, wherein the cancer is pancreatic cancer.

68. A method according to claim 41, wherein the cancer is melanoma cancer.

69. A method according to claim 41, wherein the cancer is brain cancer.

70. A method according to claim 41, wherein the cancer is renal cancer.

71. A method according to claim 41, wherein the cancer is prostate cancer.

* * * * *